US010568961B2

(12) United States Patent
Kishen et al.

(10) Patent No.: US 10,568,961 B2
(45) Date of Patent: *Feb. 25, 2020

(54) PHOTOSENSITISING COMPOSITION AND ITS USES

(75) Inventors: Anil Kishen, York, PA (US); Saji George, York, PA (US)

(73) Assignee: DENTSPLY SIRONA Inc., York, PA (US)

( * ) Notice: Subject to any disclaimer, the term of this patent is extended or adjusted under 35 U.S.C. 154(b) by 305 days.

This patent is subject to a terminal disclaimer.

(21) Appl. No.: 12/936,126

(22) PCT Filed: Apr. 6, 2009

(86) PCT No.: PCT/SG2009/000126
§ 371 (c)(1),
(2), (4) Date: Oct. 1, 2010

(87) PCT Pub. No.: WO2009/123575
PCT Pub. Date: Oct. 8, 2009

(65) Prior Publication Data
US 2011/0027384 A1   Feb. 3, 2011

Related U.S. Application Data

(60) Provisional application No. 61/042,319, filed on Apr. 4, 2008.

(51) Int. Cl.
*A61K 41/00*   (2006.01)
*A61K 6/00*   (2006.01)
*A61K 9/00*   (2006.01)

(52) U.S. Cl.
CPC ........ *A61K 41/0038* (2013.01); *A61K 6/0035* (2013.01); *A61K 6/0052* (2013.01); *A61K 6/0058* (2013.01); *A61K 9/0063* (2013.01); *A61K 41/0057* (2013.01)

(58) Field of Classification Search
CPC .............. A61K 41/0057; A61K 6/0035; A61K 6/0052; A61K 6/0058; A61K 9/0063
See application file for complete search history.

(56) References Cited

U.S. PATENT DOCUMENTS

| 2005/0232953 | A1 | 10/2005 | Barnikol et al. | |
|---|---|---|---|---|
| 2006/0134186 | A1* | 6/2006 | Carlton et al. | 424/449 |
| 2006/0234959 | A1* | 10/2006 | Biel et al. | 514/28 |
| 2009/0285766 | A1* | 11/2009 | Kishen | A61K 8/34 424/49 |

FOREIGN PATENT DOCUMENTS

| WO | WO 2005/032459 | 4/2005 |
|---|---|---|
| WO | WO 2005/110340 | 11/2005 |
| WO | WO 2006/038802 | 4/2006 |
| WO | WO 2006/038803 | 4/2006 |
| WO | WO 2006/047868 | 5/2006 |
| WO | WO 2006/135344 | 12/2006 |

OTHER PUBLICATIONS

Engineer's Toolbox [downloaded Nov. 20, 2012 from the online site http://www.engineeringtoolbox.com/specific-gravity-liquids-d_336.html]).*
Remy et al., "Red blood cell substitutes: fluorocarbon emulsions and haemoglobin solutions," Brit Med Bull 55: 277-298 (1999).*
Ibers, JA et al., Science 145:920-921 (1964).*
Battino, R., et al.: "The Solubility of Oxygen and Ozone in Liquids", J. Phys. Chem. Ref.Data., vol. 12(2), pp. 163-178, 1983.
Economou-Stamatelopoulou, C., et al.: "Antibacterial Activity of Intraoculary Used Liquids Against Two Strains of Pseudomonas Aeruginosa," Ophthalmologica, 2003, 217: 426-430.
Dougherty, W.J., et al.: "Black-Pigmented Bacteria in Coronal and Apical Segments of Infected Root Canals," Journal of Endodontics, May 1998, vol. 24(5): 356-358.
Detty, M. R., et al.: "Current Clinical and Preclinical Photosensitizers for Use in Photodynamic Therapy," Journal of of Medicinal Chemistry, Jul. 29, 2004, vol. 47(16): 3897-3915.
George, S. and Kishen, A.: "Photophysical, Photochemical, and Photobiological Characterization of Methylene Blue Formations for Light-Activated Root Canal Disinfection," Journal of Biomedical Optics, May/Jun. 2007, vol. 12(3): 034029-1-034029-10.
George, S. and Kishen, A.: "Advanced Noninvasive Light-Activated Disinfection: Assessment of Cytotoxicity on Fibroblast Versus Antimicrobial Activity Against Enterococcus Faecalis," Journal of Endodontics, May 2007, vol. 33(5): 599-602.
Whitney, J.D.: "Physiologic Effects of Tissue Oxygenation on Wound Healing," Heart & Lung, Sep. 1989, vol. 18: 466-476.
Jefferson, K. K.: "What Drives Bacteria to Produce a Biofilm?," FEMS Microbiology Letters, 2004, vol. 236: 163-173.
Kishen, A., et al.: "Entercocccus Faecalis-Mediated Biomineralized Biofilm Formation on Root Canal Dentine In Vitro," Journal of Biomedical Materials Research, 2006, vol. 77(2): 406-415.
Pervaiz, S.: "Reactive Oxygen-Dependent Production of Novel Photochemotherapeutic Agents," FASEB Journal, Mar. 2001, vol. 15(3): 612-617.
Soncin, M., et al.: "Approaches to Selectivity in the Zn(II)-Phthalocyanine-Photosensitized Inactivation of Wild-Type and Antibiotic-Resistant *Staphylococcus aureaus*," Photochemical & Photobiological Sciences, 2002, vol. 1: 815-819.
Soukos, N. S., et al.: "Targeted Antimicrobial Photochemotherapy," Antimicrobial Agents and Chemotherapy, Oct. 1998, vol. 42(10): 2595-2601.
Yoshida, H. et al.: "Heavy Fluorocarbon Liquids for a Phase-Conjugated Stimulated Brillouin Scattering Mirror," Applied Optics, Jun. 1, 1997, vol. 36(16): 3739-3744.

* cited by examiner

*Primary Examiner* — John Pak
(74) *Attorney, Agent, or Firm* — Dentsply Sirona Inc.

(57) ABSTRACT

The present invention provides a photosensitising composition comprising a mixture of at least one oxygen carrier, at least one oxidising agent and at least one surfactant, and its uses. The ratio of the at least one oxygen carrier to the at least one oxidising agent to the at least one surfactant may be in the range of 50:40:10 to 80:19.8:0.2. The photosensitising composition may be used for treating and/or preventing conditions caused by microorganisms.

18 Claims, 7 Drawing Sheets

PHOTOSENSITISING COMPOSITION AND ITS USES

This application is a U.S. National Stage application of PCT international application number PCT/SG2009/000126, which was filed on Apr. 6, 2009 and claims the benefit of U.S. provisional patent application no. 61/042,319, which was filed on Apr. 4, 2008.

FIELD OF THE INVENTION

The present invention provides a photosensitising composition. The photosensitising composition may be used for inactivating bacteria. The present invention also provides uses of the photosensitising composition.

BACKGROUND OF THE INVENTION

Recent advances in the application of photodynamic therapy (PDT) are showing great potential in the treatment of infections involving localised bacterial growth. The killing of bacteria by PDT involves the use of a photosensitiser and low-level light for treating localised bacterial infections. During PDT, the photoactivated photosensitiser molecule can either transfer an electron to the neighbouring molecule (i.e. Type-I reaction), where the electron transfer reactions between the triplet state sensitizer and biomolecules result in the generation of several radical species which can cause cell damage, or by a type-II reaction, where the energy transfer from triplet state species to molecular oxygen produces singlet oxygen ($_1O^2$), a highly reactive species causing cell death.

The activation of photosensitizers in the presence of oxygen results in the production of reactive oxygen species, involving hydroxyl radicals, superoxides and singlet oxygen. The oxygen based free radicals, involved in the photo oxidised inactivation of microorganisms acts on multiple targets resulting in instantaneous killing. This aspect of PDT makes the selection of photoresistant microbial strain highly unlikely. Production of highly reactive singlet oxygen capable of destroying biomolecules has been identified as the principle agent causing bacterial killing.

WO 2006/135344 teaches a composition that comprises a mixture of glycerol, ethanol and water, preferably in the ratio 30:20:50 by volume. This composition enables the photosensitizer deep into the dentinal tubules and the anatomical complexities of the tooth, releases significantly high singlet oxygen when activated, better uptake by the bacterial cells with less tendency for surface aggregation and also causes more severe destruction of bacterial cells (membrane damage and DNA damage). Photosensitizer, when dissolved in this formulation, when used along with an oxygen carrier, which also acts as a liquid optical conduit (perfluorodecahydro naphthalene) is able to eliminate bacteria more significantly from the root canal system (George S and Kishen A, J Biomed Opt, 2007; George S and Kishen A, J. Endod., 2007). Although this approach is advantageous in inactivating short-span, i.e. 2 days to 1 week, biofilms, it was not able to inactivate matured long-span biofilms (Kishen A et al, J Biomed Mater Res A, 2006). The primary factors that make inactivation of biofilm bacteria difficult are: (1) limited photosensitizer diffusion into the biofilm structure, (2) lack of proper oxygen tension in the interior of the biofilm, and (3) difficulty in ensuring proper light propagation through biofilm due to scattering and absorption of light.

There is therefore a need in the art for an improved photosensitising composition which is able to inactivate matured long-span biofilms.

SUMMARY OF THE INVENTION

The present invention seeks to address the problems above, and in particular provides a new photosensitising composition and its uses thereof. In particular, there is provided a photosensitising composition comprising a mixture of: at least one oxygen carrier, at least one oxidising agent, and at least one surfactant. The composition may further comprise at least one photosensitising compound.

According to a first aspect, the present invention provides a photosensitising composition comprising a mixture of: at least one oxygen carrier; at least one oxidising agent; and at least one surfactant, wherein the ratio of the volume of the at least one oxygen carrier to the at least one oxidising agent to the at least one surfactant is in the range of 50:40:10 to 80:19.8:0.2. In particular, the ratio may be from 60:39:1 to 76:23.6:0.4. Even more in particular, the ratio is 75:24.5:0.5. According to a particular aspect, the photosensitising composition may be in the form of an emulsion.

Any suitable oxygen carrier, oxidising agent and surfactant may be used for the purposes of the present invention. For example, the at least one oxygen carrier may be selected from the group consisting of: perfluorodecahydro naphthalene, perfluorodecalin, perfluorohexane, octafluoropropane, perfluorobutane, perfluorooctane, perfluoromethyldecalin and $O_2IrCl(CO)(P[C_6H_5]_3)_2$. For example, the at least one oxidising agent may be selected from the group consisting of: hydrogen peroxide, dilute sodium hypochlorite, DMSO and chlorine dioxide. For example, the at least one surfactant may be selected from the group consisting of: mineral oil, glycerol, polyethylene glycol, non-ionic detergent, polypropylene glycol and SDS. In particular, the non-ionic detergent may be Triton X. Even more in particular, the surfactant is Triton X-100.

According to a particular aspect, the present invention provides a photosensitising composition comprising a mixture of perfluorodecahydro naphthalene, hydrogen peroxide and Triton X. According to another particular aspect, the ratio of the volume of perfluorodecahydro naphthalene to hydrogen peroxide to Triton X may be 75:24.5:0.5.

The photosensitising composition according to any aspect of the present invention may further comprise at least one photosensitising compound. Any suitable photosensitising compound may be used for the purposes of the present invention. For example, the at least one photosensitising compound may be selected from the group consisting of: toluidene blue, methylene blue, arianor steel blue, tryptan blue, crystal violet, azure blue cert, azure B chloride, azure 2, azure A chloride, azure B tetrafluoroborate, thionin, azure A eosinate, azure B eosinate, azure mix sicc, azure II eosinate, haematoporphyrin HCl, haematoporphyrin ester, aluminium disulphonated phthalocyanine, chlorins, photoactive fullerenes (e.g. C16-b), aminolevulinic acid (ALA), bacteriochlorins, phthalocyanines, pheophorbides, purpurins, naphthalocyanines, indocyanine green, or mixtures thereof. In particular, the at least one photosensitising compound is methylene blue.

According to a particular aspect of the present invention, the photosensitising composition may further comprise a mixture of polyethylene glycol, ethanol and water. In particular, the photosensitising composition may further comprise a mixture of glycerol, ethanol and water. Even more in particular, the ratio of the volume of the polyethylene glycol to ethanol to water is 30:20:50.

The photosensitising composition may further comprise a pharmaceutically acceptable excipient and/or carrier.

According to a particular aspect, the photosensitising composition may be formulated for use in oral cavity treatment. The composition may be formulated for use in the treatment and/or prevention of conditions caused by microorganisms. The composition may be formulated for use in the treatment and/or prevention of periodontal and/or halitosis conditions. The composition may also be formulated for topical administration or administration by injection. The composition may be formulated as an oral rinse, a mouthwash and/or an atomizing spray.

According to a further aspect, the photosensitising composition according to any aspect of the present invention may be for use in medicine.

The present invention also provides a use of a photosensitising composition according to any aspect of the present invention in the manufacture of a medicament for treating and/or preventing conditions caused by microorganisms in a subject, the treatment and/or prevention comprising the steps of:
(a) administering the photosensitising composition; and
(b) irradiating the area to which the composition is administered with light at a wavelength absorbed by a photosensitising compound.

The medicament may be for treating and/or preventing conditions caused by microorganisms in the oral cavity of a subject. For example, the medicament may be for treating and/or preventing periodontal and/or halitosis conditions. For example, the conditions may include, but are not limited to, gingivitis, periodontitis dental caries, root caries, root canal infection, apical periodontitis and the like. The medicament may also be for managing bacteria deep within dental caries lesions. The medicament may also be used to eliminate bacterial biofilm in any localised infection. In particular, the medicament may be used for elimination and inactivation of mature long-span biofilms.

The present invention also provides a method of treating and/or preventing conditions caused by microorganisms in a subject, wherein the method comprises the steps of:
(a) administering a photosensitising composition according to any aspect of the present invention; and
(b) irradiating the area to which the composition is administered with light at a wavelength absorbed by a photosensitising compound.

The method may be for treating and/or preventing conditions caused by microorganisms in the oral cavity of a subject. For example, the method may be for treating and/or preventing periodontal and/or halitosis conditions. For example, the conditions may include, but are not limited to, gingivitis, periodontitis dental caries, root caries, root canal infection, apical periodontitis and the like. The method may also be for managing bacteria deep within dental caries lesions. The method may also be used to eliminate bacterial biofilm in any localised infection. In particular, the method may be used for elimination and inactivation of mature long-span biofilms.

The irradiation of step (b) may be carried out for a time period of 30 minutes or less. For example, the irradiation of step (b) may be carried out for 10 seconds to 30 minutes. The time period for carrying out the irradiation of step (b) depends on the type of photosensitising compound used and the type of light used. In particular, the irradiation of step (b) may be carried out for a time period of 5 minutes to 15 minutes. Even more in particular, the irradiation of step (b) is carried out for a time period of 10 minutes.

The dose of light used in step (b) may range from 10 $J/cm^2$ to 200 $J/cm^2$. In particular, the dose of light used in step (b) ranges from 50 $J/cm^2$ to 150 $J/cm^2$.

The light used in step (b) may have any suitable wavelength. For example, the wavelength of the light depends on the type of photosensitising compound's absorbance maxima. The wavelength of the light may range from the visible to the near infra-red range of wavelength. The light used in step (b) may have a wavelength ranging from about 400 nm to about 1400 nm. In particular, the light use may have a wavelength ranging from about 600 nm to about 900 nm. In particular, the light used in step (b) has a wavelength ranging from about 650 nm to about 800 nm. Even more in particular, the light used in step (b) has a wavelength of 660 nm.

The present invention also provides a kit for treating and/or preventing conditions caused by microorganisms in a subject, the kit comprising a photosensitising composition according to any aspect of the invention, disposed in at least one suitable container. The photosensitising composition may comprise at least one photosensitising compound. The kit may be for treating and/or preventing conditions caused by microorganisms in the oral cavity of a subject. For example, the kit may be for treating and/or preventing periodontal and/or halitosis conditions. For example, the conditions may include, but are not limited to, gingivitis, periodontitis dental caries, root caries, root canal infection, apical periodontitis and the like. The kit may also be used for managing bacteria deep within dental caries lesions. The kit may also be used to eliminate bacterial biofilm in any localised infection. In particular, the kit may be used for elimination and inactivation of mature long-span biofilms.

The kit may further comprise at least one light emitting device capable of emitting light at a wavelength absorbed by a photosensitising compound.

The present invention also provides a method of preparing the composition according to any aspect of the invention. The method may comprise the step of: (a) preparing a mixture of at least one oxygen carrier; at least one oxidising agent; and at least one surfactant, wherein the ratio of the volume of the at least one oxygen carrier to the at least one oxidising agent to the at least one surfactant is in the range of 50:40:10 to 80:19.8:0.2. In particular, the mixture of the at least one oxygen carrier, at least one oxidising agent, and at least one surfactant is prepared by sonicating or vortexing the at least one oxygen carrier, at least one oxidising agent, and at least one surfactant.

The method may further comprise the step of adding at least one photosensitising compound to the mixture of step a). The method may further comprise the step of adding polyethylene glycol, ethanol and water to the mixture of step a). In particular, the volume of polyethylene glycol, ethanol and water is added in the ratio of 30:20:50.

DETAILED DESCRIPTION OF THE INVENTION

Figure 1:
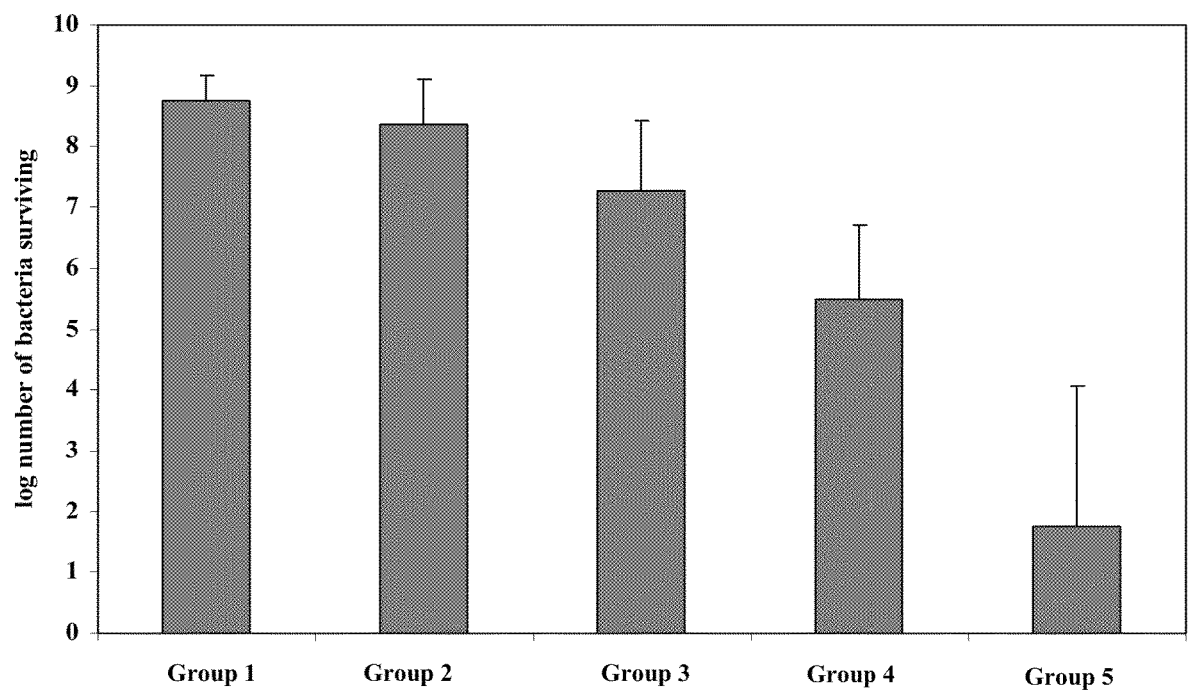
FIG. 1 shows bacteria surviving different treatments on matured 4-week old biofilm.

Bibliographic references mentioned in the present specification are for convenience listed in the form of a list of references and added at the end of the examples. The whole content of such bibliographic references is herein incorporated by reference.

Bacterial biofilm in the root canal system that evoke inflammatory response can lead to apical periodontitis. Conventionally, disinfection of the root canal is sought by a 'chemo-mechanical' approach that involves cleaning and shaping of the root canal system by the application of chemical disinfectant and mechanical instrumentation. Nonetheless, this technique often fails to eradicate bacterial biofilms completely; mostly due to various microbiological and anatomical factors. Endodontic pathogens such as *Enterococcus faecalis* have been reported to form biofilm even on medicated root canals which is regarded as one of the reasons for its persistence in the post treatment endodontic environment. The phenotypic and genotypic variation of biofilm-bacteria when compared to their 'free-floating' counterparts, complemented by the structure and composition of biofilm matrix, contribute to their high antimicrobial resistance. *Enterococcus faecalis* has the ability to penetrate into the dentinal tubules and form distinct mineralized biofilm within the root canal. As mentioned above, although the composition described in WO 2006/135344 was considered to be more effective than conventional photodynamic therapy (PDT), the bactericidal effect was significantly less in matured biofilm models. The increased thickness and calcification of matured biofilm matrix was thought to contribute to its resistance. A matured biofilm matrix is such as one described in Kishen A et al, J Biomed Mater Res A., 2006.

Therefore, an ideal photosensitising composition or formulation for PDT in root canal infection should allow: (a) penetration of the photosensitiser deep into the dentinal tubules and anatomical complexities of the root canal; (b) improve the photophysical characteristics of the photosensitiser; (c) supply adequate amount of oxygen; (d) minimise scattering of light by dentine; and (e) enables conduction or transmission of light with minimal energy loss deep into the dentine tissue.

The present invention provides a photosensitising composition and its uses thereof. In particular, there is provided a photosensitising composition comprising a mixture of: at least one oxygen carrier; at least one oxidising agent; and at least one surfactant. The photosensitising composition may further comprise at least one photosensitising composition.

According to one aspect, the present invention provides a photosensitising composition comprising a mixture of: at least one oxygen carrier; at least one oxidising agent; and at least one surfactant, wherein the ratio of the volume of the at least one oxygen carrier to the at least one oxidising agent to the at least one surfactant is in the range of 50:40:10 to 80:19.8:0.2. In particular, the volume ratio may be from 60:39:1 to 76:23.6:0.4. Even more in particular, the ratio is 75:24.5:0.5.

For the purposes of the present invention, a 'photosensitising composition' is defined as a photosensitising composition which may or may not include a photosensitising compound. In particular, the photosensitising composition may or may not comprise an exogenous photosensitiser. For example, endogenous pigments of bacteria may be utilised as a photosensitising compound. Further examples are provided below. Such bacteria are common in root canal infections. Accordingly, a photosensitising compound may not be required in the photosensitising composition.

The photosensitising composition may be in any suitable form. For example, the photosensitising composition may be in the form of an emulsion. The emulsion may be formed by any suitable method. For example, the emulsion may be formed by rigorously mixing the photosensitising composition. In particular, the emulsion may be formed by sonicating or vortexing the at least one oxygen carrier, at least one oxidising agent, and at least one surfactant. The oxidising capacity of the photosensitising composition may be increased when the composition is in the form of an emulsion.

Since the root apex and greater depth of dentinal tubules is considered as being a hypoxygenic physiologic site, oxygen carriers such as perfluorocarbons (PFCs) may increase the performance of PDT. PFCs are chemically and biochemically inert due to the strong intra-molecular bonding (C—F bonds are 485 kJ/mol, that is 84 kJ/mol more than a regular C—H bond). The chemical structure and the weak intermolecular interactions are responsible for the specific properties of PFCs, namely the low surface tensions (<20 mN/m), dielectric constants and refractive indices, the high densities, viscosities and gas solubility that are the largest known for liquids. At present, PFCs are used in tissue oxygenation fluids (blood substitutes, oxygen therapeutics), as anti-tumour agents, perfusates for isolated organs, surgical tools for ophthalmology, lubrication and cushioning for particular disorders, as cell culture media supplements and in drug formulations and delivery. The oxygen carrier increases the half life of the singlet oxygen. Any suitable oxygen carrier may be used for the present invention. The at least one oxygen carrier may be a synthetic molecular oxygen carrier. For example, the oxygen carrier may be hydroperfluoro carbons, perfluoro carbons or a mixture thereof. Particular examples include, but are not limited to, perfluorodecahydro naphthalene, perfluorodecalin, perfluorohexane, octafluoropropane, perfluorobutane, perfluorooctane, perfluoromethyldecalin and $O_2IrCl(CO)(P[C_6H^5]_3)_2$. In particular, the at least one oxygen carrier is perfluorodecahydro naphthalene.

The at least one oxidising agent may aid in neutralising bacteria, digesting polymeric biofilm matrix and also enhancing other oxygen based free radical generation. The oxidising agent may also pre-activate the photosensitising compound, and hence shorten the duration of the PDT. However, the oxidising agent may be added in a suitable concentration as application of oxidising agents at very high concentrations may raise serious safety issues because of their potential toxicity. Any suitable oxidising agent may be used for the purposes of the present invention. For example, the at least one oxidising agent is selected from the group consisting of: hydrogen peroxide, dilute sodium hypochlorite, DMSO and chlorine dioxide. In particular, the at least one oxidising agent is hydrogen peroxide.

The use of surfactants may improve the penetrability of photosensitisers into the complexities of the root canal and dentinal tubules. The surfactant also disrupts the bacterial membrane, in the case of gram negative bacteria and ensures the photosensitiser compound uptake into bacterial cells. For example, the use of hydrophilic and/or surfactant containing medium may improve the use of the photosensitising composition in PDT. Surfactants facilitate penetrability of the photosensitizing composition into the root canal complications and reach the apical foramen of the tooth. The surfactants reduce the surface tension and therefore, enhance the penetrability of the photosensitising solution.

Any suitable surfactant may be used for the present invention. For example, the at least one surfactant may be a trihydric alcohol or a polyester. The at least one surfactant may be a refractive index matching liquid. The polyester may be polyethylene glycol or polypropylene glycol. The trihydric alcohol may be glycerol. For example, the at least one surfactant may be selected from the group consisting of: mineral oil, glycerol, polyethylene glycol, non-ionic detergent, polypropylene glycol, SDS and any detergent suitable for use for the present invention. The non-ionic detergent may be Triton X. In particular, the at least one surfactant is Triton X. Even more in particular, the at least one surfactant is Triton X-100.

According to a particular aspect of the present invention, the photosensitising composition comprises a mixture of perfluorodecahydro naphthalene, hydrogen peroxide and Triton X. Even more in particular, the photosensitising composition may comprise a mixture of perfluorodecahydro naphthalene, hydrogen peroxide and Triton X-100. The ratio of the volume of perfluorodecahydro naphthalene to hydrogen peroxide to Triton X in the mixture may be in the range of 50:40:10 to 80:19.8:0.2. In particular, the ratio is from 60:39:1 to 76:23.6:0.4. Even more in particular, the ratio is 75:24.5:0.5.

The photosensitising composition of the present invention may also comprise a refractive index matching liquid. In particular, the composition comprises a high refractive index liquid medium. The refractive index liquid medium may create a liquid wave guide in the dentine. The unique structural and optical characteristics of the dentine tissue is utilised in combination with a high refractive index liquid medium such as glycerol or mineral oil to achieve a liquid optical-conduit (waveguide)-effect in root canal lumen and dentinal tubules. The optical-waveguide-effect will aid in diminishing dentine tissue scatter and in addition, the higher refractive index of the medium, when compared to the dentine, will enable achieving predominantly total internal reflection and better light energy distribution within the root canal lumen (and anatomical complexities) and the dentinal tubules. High refractive index liquids such as glycerol and mineral oil minimise tissue scatter and obtain total internal reflection within the root canal lumen and dentinal tubules. Therefore, a suitable liquid, or mixtures thereof, will be one that can provide ideal refractive index to transform root canal lumen and dentinal tubular spaces into optical conduit.

The composition of the present invention may further comprise at least one photosensitising compound. The at least one photosensitising compound comprised in the photosensitising composition may be any suitable photosensitising compound. For the purposes of the present invention, the terms 'photosensitising compound' and 'photosensitiser' may be used interchangeably. A suitable choice of a photosensitiser should preferably have certain characteristics. The photosensitiser must have the ability to selectively accumulate in target areas, for example, cancerous and/or pre-cancerous tissues. In other words, while it is eliminated from normal tissue, it is retained in cancerous tissue and/or pre-cancerous cells. Further, from the point of view of localisation in target areas, for example in periodontal areas or in tumours, the best photosensitisers are those that are hydrophobic in order for them to penetrate cell membranes more readily. However, if the photosensitisers are to be administered intravenously, the photosensitisers should be at least partially water soluble and therefore, also hydrophilic, to disperse in the blood stream. Therefore, combining the two requirements, it is preferable to use a photosensitiser which is amphiphilic. Alternatively, the photosensitiser may be modified to have amphiphilic properties by chemically modifying a fundamentally hydrophobic photosensitiser by attaching polar residues such as amino acids, sugars and/or nucleotides.

The photosensitiser should also be capable of absorbing light at a wavelength in the in the region of maximum transparency of biological tissues. This would allow light to penetrate deeper in the tissue to activate the photosensitiser. This is particularly useful if the target area is deep and it is desired for the photosensitiser to reach the target area effectively. For example, malignant tissues which are deep would require the photosensitiser to absorb light at a long wavelength. However, wavelengths longer than 900 nm are energetically too low to provide sufficient energy required for the excitation of triplet oxygen to its singlet state in PDT.

A suitable photosensitiser should also be able to exhibit minimum toxicity in the dark in order for light activation of the drug to produce maximum benefits without side effects derived from the inherent toxicity. Further, the photosensitiser should have a high yield of triplet-state formation and a long triplet lifespan. In other words, the non-radiative intersystem crossing from the excited singlet state of the photosensitiser to its excited triplet state should be efficient compared to the direct radiative transition (fluorescence) from the excited singlet state. A longer triplet lifespan would enhance the chance of producing a cytotoxic reagent or a cytotoxic reaction from the excited state.

The photosensitiser should also not aggregate since aggregation can reduce the extinction coefficient and shorten the lifespan and quantum yield of the excited triplet state. Aggregated forms of photosensitiser can also affect its pharmacokinetics and biodistribution. The photosensitiser should also be able to rapidly excrete from the body of the subject it is administered to. This will produce low systemic toxicity and will reduce sunlight sensitivity following PDT.

Examples of photosensitisers include porphyrin derivatives. The first group of photosensitisers used in clinical PDT was hematoporphyrin derivatives. Photofrin® (herein referred to as Photofrin), a photosensitiser obtained from hematoporphyrin by treatment with acids is approved by the U.S. Food and Drug Administration, as well as by other regulatory agencies throughout the world for the treatment of a variety of malignant tumours. Photofrin is actually a complex mixture consisting of various derivatives, as well as dimeric and oligomeric fractions. In commercial Photofrin, the fractions are partly purified to be around 85% oligomeric materials. Because Photofrin is a complex mixture, there are still concerns about the identity of the active components and the reproducibility of the synthetic process producing it. Photofrin is a non-toxic drug. However, the disadvantage is that it is retained for some time by the skin. For this reason, patients are required to avoid direct sunlight, very bright artificial lights or strong residential indoor lighting for a period of 4 to 6 weeks after injection of the drug.

In order to prepare "second-generation" photosensitisers that consist of pure single components (as opposed to a mixture comprising Photofrin), and be capable of absorbing light at a wavelength further in the red region to provide deeper penetration in tissues, efforts have already led to many promising compounds for use as photosensitisers. These include modified porphyrins, chlorins, bacteriochlorins, phthalocyanines, naphthocyanines, pheophorbides, and purpurins (Dougherty W J et al, 1998; Detty M R et al, 2004).

Chlorins and bacteriochlorins are attractive because of their ability to absorb longer wavelength. However, these classes of drugs undergo re-aromatisation of the pyrrole rings to produce porphyrins, which limit their lifetime in vivo as photosensitisers. Further, none of these classes of materials have been FDA approved specifically for cancer treatment.

Another example of a photosensitiser is 5-Aminolaevulinic Acid (ALA). ALA is a metabolic precursor in the biosynthesis of hematoporphyrin, which endogenously generates an effective photosensitiser, protoporphyrin IX. It thus provides an alternative to the administration of an exogenous photosensitiser. Even though ALA can be endogenously generated from glycine and succinyl CoA, exogenous administration of ALA is chosen for a controlled build-up of protoporphyrin IX. The advantages offered by ALA-induced protoporphyrin IX over Porphyrin are: (1) ability to reach optimum therapeutic ration in 4-6 hours; (2) rapid systemic clearance of the photosensitiser within 24 hours, thus not only eliminating prolonged skin photosensitivity, but also allowing repeated treatment every 24 hours; and (3) accurate analysis of photosensitiser levels by in situ monitoring of its fluorescence. However, the limitation of ALA stems from its hydrophilic nature, which restricts its penetration through keratinous lesion of normal skin. For this reason lipophilic ALA esters may be preferable because they can penetrate cells more readily.

Yet another type of photosensitisers are phthalocyanines and naphthalocyanines. These are another class of PDT photosensitisers that absorb light in the long wavelength region of between 670 nm and 780 nm, and exhibit high molar extinction coefficient. These photosensitisers are hydrophobic in nature and exhibit limited solubility. Their solubility can be enhanced by attaching sulfonic acid, carboxylic acid or amino acid groups to the ring. Clinical evaluation of sulfonated phthalocyanine for use in PDT has been further motivated by its negligible dark toxicity, its minimal skin photosensitivity and its ability to be photoactivated at a much longer wavelength. The phthalocyanines and naphthalocyanines are already in the early stages of preclinical and clinical evaluations. However, a problem encountered with these compounds is their tendency to aggregate in aqueous media at relatively low concentrations, resulting in a loss of their photoactivity.

Cationic photosensitisers are also suitable. This class of photosensitisers carries a positive charge on the heteroatom of the ring structure. These cationic PDT photosensitisers tend to be bound intracellularly. Another distinction is that some of these photosensitisers (e.g. rhodamine 123 (Rh-123)) are selectively taken up by the mitochondria of living cells. Methylene blue (basic dye) is a cationic photosensitiser, which is currently in clinical use. It is important to note that the surfaces of bacterial cells are negatively charged and basic photosensitisers or dyes, which are positively charged, are most often used in staining cells in bacteriology.

For the purposes of the present invention, any suitable photosensitiser may be used. The photosensitising composition of the present invention may comprise at least one photosensitising compound. For example, the at least one photosensitising compound may be selected from the group consisting of: toluidene blue, methylene blue, arianor steel blue, tryptan blue, crystal violet, azure blue cert, azure B chloride, azure 2, azure A chloride, azure B tetrafluoroborate, thionin, azure A eosinate, azure B eosinate, azure mix sicc, azure II eosinate, haematoporphyrin HCl, haematoporphyrin ester, aluminium disulphonated phthalocyanine, chlorins, photoactive fullerenes (e.g. C16-b), aminolevulinic acid (ALA), bacteriochlorins, phthalocyanines, pheophorbides, purpurins, naphthalocyanines, indocyanine green, or mixtures thereof. In particular, the at least one photosensitising compound is methylene blue.

According to a particular aspect, the photosensitising composition may further comprise a mixture of: at least one further surfactant; at least one alcohol; and/or water, wherein the ratio of the volume of the at least one further surfactant to the at least one alcohol to water is in the range of 10:5:85 to 40:30:30, with the proviso that when the at least one further surfactant is an alcohol, it is different from the at least one alcohol. The volume ratio may be in the range of 15:10:75 to 35:25:40. Even more in particular, the ratio is 30:20:50.

In particular, the surfactant may be a polyethylene glycol. According to a particular aspect, the photosensitising composition may further comprise a mixture of a polyethylene glycol, an alcohol and water. Any suitable alcohol may be used for the purposes of the present invention. For example, the alcohol may be a monohydric alcohol. The alcohol may also be a dihydric alcohol and/or a trihydric alcohol. A monohydric alcohol contains only one hydroxyl group in each molecule. Examples of monohydric alcohols include, but are not limited to, methanol, ethanol, propanol, butanol, pentanol, hexacecanoyl, melissyl alcohol and the like. Further, the monohydric alcohol may be a primary, secondary or tertiary alcohol. Examples of dihydric alcohols include glycols and diols. Examples of trihydric alcohols include glycerol. In particular, the alcohol is ethanol. According to another particular aspect, the photosensitising composition further comprises a mixture of glycerol, ethanol and water. The ratio of the volume of glycerol to ethanol to water in the mixture may be in the range of 10:5:85 to 40:30:30. In particular, the ratio is in the range of 15:10:75 to 35:25:40. Even more in particular, the ratio is 30:20:50.

The photosensitising composition of the present invention may further comprise other compounds in order to make the composition more suitable for use as a photosensitising composition in PDT. The photosensitising composition of the present invention may be adapted to better eliminate bacteria and/or microorganisms. In particular, the photosensitising composition may be better suited for eliminating bacteria and/or microorganisms within the anatomical complexities of the root canals and reach deeper into the dentinal tubules. Accordingly, the photosensitising composition may further comprise at least one polycationic compound. Limitation in photosensitiser uptake by microbial cells is a potential problem associated with PDT mediated bacterial killing. The limited killing of gram negative bacteria has been associated with the presence of outer membrane that acts as a functional and physical barrier between the cell and the surrounding environment. However, use of polycationic compounds such as poly L-Lysine, either coupled with the photosensitiser or co-administered, can facilitate the movement of the photosensitiser across the outer membrane of the gram negative bacteria. Polycationic compounds interact with divalent cation-binding sites on cell surface lipopolysaccharides (LPS) and displace these ions. This disrupts the normal barrier property of the outer membrane causing transient 'cracks' which permits passage of hydrophobic compounds such as photosensitisers. Accordingly, in order to improve the binding of photosensitisers with bacterial cells, it may be required to attach charged, hydrophobic and/or polymers to the photosensitisers.

The addition of polycationic compounds to the photosensitising composition of the present invention may further improve the performance on the photosensitising composition in PDT. Hydrophobic and cationic photosensitisers are found to bind well with bacterial cells. Interestingly, when PDT is conducted against bacteria in the presence of mammalian cells, the mammalian cells are not affected by the PDT, killing only bacteria at lower concentrations of photosensitiser (Soncin M et al, 2002). Further, the selectivity of bacteria can be improved by coupling the photosensitiser to a polypeptide chain of lysine, which can target bacterial cells (Soukos N S et al, 1998) (Gram negative and Gram positive) bearing negative charges on the outer surface. Since the mammalian cells take up macromolecule such as polypeptide by endocytosis, a temporal selectivity may be achieved if photosensitisation is performed for a shorter duration. Examples of polycationic compounds that may be used for the present invention include, but are not limited to, cationic polypeptides such as poly L-lysine, L-arginine, D-arginine, and multivalent cations such as calcium chloride, calcium hydroxide and magnesium chloride (Soukos N S et al, 1998).

According to another particular aspect of the present invention, it provides for the utilisation of endogenous pigments of bacteria as the at least one photosensitising compound. For example, many obligatory anaerobes are found to have endogenous pigment (e.g. *Porphyromonas* species, *Bacteroides* species) such as porphyrin. These bacterial pigments may be utilised as endogenous photosensitisers to achieve the killing of the bacteria during PDT. In this approach only optimum light energy at specific wavelength is required. An additional photosensitiser (exogenous photosensitiser) is not required. These groups of bacteria are common and dominant group in root canal infections, particularly in the apical region of the root canal (deeper aspect close to the root tip). Accordingly, a photosensitising compound may not be required to be included in the photosensitising composition.

The photosensitising composition according to the present invention may further comprise a pharmaceutically or pharmacologically acceptable excipient, diluent and/or carrier. The phrase "pharmaceutically or pharmacologically acceptable" refers to molecular entities and compositions that do not produce an adverse, allergic or other untoward reaction when administered to an animal, or a human, as appropriate. The photosensitising compositions of the present invention may be an aqueous composition, optionally comprising an effective amount of the photosensitising compound, dissolved or dispersed in a pharmaceutically acceptable carrier or aqueous medium. An example of a suitable carrier includes water, such as distilled water or demineralised water, preferably pyrogen-free, sterile water or water for injection. The photosensitising composition may additionally comprise buffers, salts for adjusting the tonicity of the composition, preservatives, gelling agents and the like. The use of such agents for pharmaceutical active substances is well known in the art.

The photosensitising composition of the present invention may be formulated according to its means of use and/or administration. For example, the photosensitising composition may be formulated for use in the treatment and/or prevention of conditions caused by microorganisms in a subject. The photosensitising composition may be formulated for use in the treatment and/or prevention of conditions caused by microorganisms in the oral cavity of a subject. The photosensitising composition may be formulated for the treatment and/or prevention of conditions such as periodontal and/or halitosis conditions.

The photosensitising composition may also be formulated for use in oral cavity treatment in a subject. The subject may be an animal or human. The photosensitising composition may be formulated such that it is accessible to the interior surfaces of the mouth, including the tongue, buccal mucosa and/or gum regions. The photosensitising composition may be formulated such that it is suitable for administering the composition topically or by injection. The photosensitising composition may also be formulated as an oral rinse, a mouthwash and/or an atomizing spray.

According to another aspect, the photosensitising composition according to the present invention may be for use in medicine. For example, the photosensitising composition may be used for the treatment and/or prevention of conditions caused by microorganisms in a subject. The photosensitising composition may be used for oral cavity treatment in a subject. In particular, the photosensitising composition may be used for the treatment of microorganisms in the oral cavity of a subject. The photosensitising composition may also be used for the prevention of microorganisms in the oral cavity of a subject. The subject may be an animal or human. The photosensitising composition may also be used for the treatment and/or prevention of conditions caused by microorganisms in the oral cavity of a subject. Examples of such conditions may include, but are not limited to, periodontal conditions and halitosis conditions. For example, the conditions include, but are not limited to, gingivitis, periodontitis dental caries, root caries, root canal infection, apical periodontitis and the like. The photosensitising composition may also be used for managing bacteria deep within dental caries lesions. In particular, the photosensitising composition may also be used to eliminate bacterial biofilm in any localised infection. Even more in particular, the photosensitising composition may be used for elimination and inactivation of mature long-span biofilms.

As stated above, the present invention is useful for the elimination of a broad spectrum of microorganisms found within the dental tissues. This mode of microbial elimination is very important keeping in mind the pores nature of dentine (because of the dentinal tubules) and the ability of microbes to penetrate into these dentinal tubules. Other major limitations associated with conventional treatment, which are circumvented in the present invention are: (1) limited penetration of chemicals into these porosities or dentinal tubules; (2) ability of precipitated calcium from the dental hard tissue to buffer the efficacy of the chemical disinfectant; (3) the anaerobic environment prevailing within the hard tissues (such dentinal tubules), which can diminish the efficacy of the photodynamic therapy; and (4) the ability of bacteria to survive in a "highly drug resistant" biofilm state inside these locations.

The photosensitising composition according to any aspect of the present invention is capable of achieving deeper diffusion of the primary photosensitising compound, such as methylene blue, into the dental tissue, such as dentine. The composition is designed to have maximum uptake of the primary photosensitising compound by the bacterial cells and minimal aggregation of the primary photosensitising compound within the medium. The photosensitising composition may further comprise a liquid conduit (LC). The liquid conduit may be added to the photosensitising composition as a separate step after a period of irradiation to minimise light scattering (found within the dentine tissue) achieve greater penetration of light energy and effective killing of bacteria. The conduit is chosen in such a way that they are transparent liquid, low refractive index (similar or slightly less than water), inert, immiscible with water (to prevent atomic absorption and less light energy loss) and can be a good source for free oxygen radical to facilitate killing of bacteria and bacterial biofilm deep within the dentine tissue. For example, perfluoro carbon compounds may be used as liquid conduits. Perfluoro carbon compounds have desirable optical quality and low absorption of light (UV-VIS-IR). They have good thermodynamic property (reduced surface tension, viscosity) and desirable chemical stability. Other important features of this compound include: (1) lack of biological activity; (2) short retention time in the body; (3) their ability to dissolve gas (especially oxygen and carbon dioxide); (4) they have antimicrobial (Economou-Stamatelopoulou C et al, 2003) and anti-inflammatory effect and has been used for wound healing (J D Whitney, 1989); and (5) facilitate better light energy delivery (Yoshida H et al, 1997).

Another aspect of the present invention is a use of the photosensitising composition according to any aspect, as described above, in the manufacture of a medicament for treating and/or preventing conditions caused by microorganisms in a subject. The subject may be an animal or a human. The treatment and/or prevention may comprise the steps of:
(a) administering the photosensitising composition according to any aspect of the present invention; and
(b) irradiating the area to which the composition is administered with light at a wavelength absorbed by a photosensitising compound.

The medicament may be for treating and/or preventing conditions caused by microorganisms in the oral cavity of a subject. For example, the medicament may be for treating and/or preventing conditions caused by microorganisms, such as periodontal conditions and halitosis conditions. The conditions may include any one of the following: gingivitis, periodontitis dental caries, root caries, root canal infection, apical periodontitis and the like. The medicament may also be for elimination of bacterial biofilm in any localised infection and/or managing bacteria deep within dental caries lesions. In particular, the medicament may be used for elimination and inactivation of mature long-span biofilms.

The photosensitising compound may be comprised in the photosensitising composition. Any suitable photosensitising compound may be used as described above.

The treatment and/or prevention may further comprise a step of waiting a predetermined period of time between steps (a) and (b) above. The step of waiting for a predetermined period of time between steps (a) and (b) may be from about 1 minute to 5 days. The waiting step may be from about 10 minutes to 3 days. The waiting step may be from 20 minutes to 1 day. The waiting step may be from 30 minutes to 5 hours. The steps described above may be repeated as often as required, for example until the condition has reduced to a desired level or has been eliminated. The steps may be repeated after intervals of predetermined periods. The interval for the repeatability of the steps would be obvious to a person skilled in the art. For example, the steps may be repeated every few hours, every day, every 2 or 3 days.

The photosensitising composition in step (a) may be administered topically or by injection. The composition may be administered to the interior surfaces of the mouth, including the tongue, buccal mucosa and/or gum regions. The composition may also be administered to any part of the oral cavity which is need of such composition.

Any suitable light may be used for the irradiation in step (b). For example, a low powered light source or a diode laser source may be used. Any suitable light such as visible or infrared lasers may be used. High energy non-visible light such as tungsten halogen or xenon arc source may also be used. LED light sources may also be used. The advantage of using LED light sources is that it will reduce the potential for the generation of uncomfortable heat, and therefore cause less discomfort to the subject. The irradiation of step (b) may be performed for the whole of the affected area. In particular, irradiation is performed for the whole interior of the mouth. For example, the light source may be manipulated such that accessible interior surfaces are irradiated. Alternatively, only some areas are irradiated. For example, individual pockets of areas may be irradiated. The light source may be adapted to irradiate all regions of the oral cavity, including under the tongue and through the flesh covered lingual, labial, anterior and posterior areas of the oral cavity and through the bite surface.

The light used in step (b) may have any suitable wavelength. The wavelength depends on the photosensitising compound used for the purposes of the present invention. The wavelength depends on the type of photosensitising compound's absorbance maxima. The wavelength of the light may range from the visible light range to the near infrared range of wavelength. The light source may have a wavelength ranging from about 400 nm to about 1400 nm. The light source may have a wavelength ranging from about 600 nm to 900 nm. In particular, the wavelength is ranging from about 650 nm to about 800 nm. Even more in particular, the wavelength is about 660 nm, or about 664 nm. The irradiation enables the activation of the photosensitising compound. Accordingly, the wavelength used for the irradiation will depend on the photosensitising compound used for the PDT. For example, if indocyanine green (ICG) is used as the photosensitising compound, a laser light of 808 nm wavelength may be used. Further, near infrared light is expected to penetrate hard tissues better. It should be noted that any non-toxic photosensitiser, and subsequently light source with optimum wavelength, will be utilised to achieve light activation.

When endogenous pigments of obligatory anaerobes are used as 'endogenous photosensitisers' without the use of additional exogenous photosensitisers, light sources at a lower range in the visible spectrum is required. For example, if the endogenous pigment porphyrin in *Porphyromonas* is used as the photosensitiser in PDT, a light of wavelength of about 400 nm would be required.

The dose of light used in step (b) may range from 10 $J/cm^2$ to 200 $J/cm^2$. In particular, the dose of light may range from 50 $J/cm^2$ to 150 $J/cm^2$.

The intensity of the light source may range from 1 to 100 mW. In particular, the intensity may range from 20 to 50 mW. Even more in particular, the intensity of the light source is about 30 mW.

The irradiation of step (b) may be carried out for any suitable period of time. For example, the irradiation is carried out for a time period of about 30 minutes or less. For example, the irradiation of step (b) may be carried out for about 10 seconds to 30 minutes. The time period for carrying out the irradiation of step (b) may depend on the type of photosensitising compound used and the type of light used. In particular, the irradiation may be carried out for a time period of about 5 minutes to 15 minutes. Even more in particular, the irradiation is carried out for about 10 minutes. The irradiation may be performed for the entire mouth of the subject or specific regions of infection, for example, at the area of caries lesion or at the root canal.

It has been found that photoproducts formed by irradiating the photosensitiser (outside biological sites) have a long lifespan and when such pre-activated photosensitiser is applied to the actual site (in the subject's body), it produces a better outcome. This type of photodynamic therapy is termed 'pre-activation' or 'pre-irradiation therapy' (Pervaiz S, 2001). The action is mediated by the photoproducts formed from the photosensitiser on irradiation which depends on the physical-chemical conditions under which the irradiation is done. This includes nature of the photoproducts, wavelength(s) used, intensity of light, temperature, oxygen and duration of irradiation. The specificity of photo products to the targets as the parental compound promises a better treatment outcome. This is of particular use when applied to tooth (dentine) since scattering and absorption of light may diminish the dosimetry of light.

Another aspect of the present invention is a method of treating and/or preventing conditions caused by microorganisms in a subject, wherein the method comprises the steps of:
(a) administering the photosensitising composition according to any aspect of the present invention; and
(b) irradiating the area to which the composition is administered with light at a wavelength absorbed by a photosensitising compound.

The method may be for treating and/or preventing conditions caused by microorganisms in the oral cavity of a subject. For example, the method may be for treating and/or preventing conditions caused by microorganisms, such as periodontal conditions and halitosis conditions. The conditions may include, but are not limited to, gingivitis, periodontitis dental caries, root caries, root canal infection, apical periodontitis and the like. The method may also be for elimination of bacterial biofilm in any localised infection and/or managing bacteria deep within dental caries lesions. In particular, the method may be for elimination and inactivation of mature long-span biofilms. The subject may be an animal or a human.

The photosensitising composition may comprise a photosensitising compound. The treatment and/or prevention may further comprise a step of waiting a predetermined period of time between steps (a) and (b) above. The step of waiting for a predetermined period of time between steps (a) and (b) may be from about 1 minute to 5 days. The waiting step may be from about 10 minutes to 3 days. The waiting step may be from 20 minutes to 1 day. The waiting step may be from 30 minutes to 5 hours.

The steps described above may be repeated as often as required, for example until the condition has reduced to a desired level or has been eliminated. The steps may be repeated after intervals of predetermined periods. The interval for the repeatability of the steps would be obvious to a person skilled in the art. For example, the steps may be repeated every few hours, every day, every 2 or 3 days.

The photosensitising composition in step (a) may be administered topically or by injection. The composition may be administered to the interior surfaces of the mouth, including the tongue, buccal mucosa and/or gum regions. The composition may also be administered to any part of the oral cavity which is need of such composition.

Any suitable light source may be used for the irradiation in step (b). For example, a low powered light source or a diode laser source may be used. Any suitable light such as visible or infrared lasers may be used. High energy non-visible light such as tungsten halogen or xenon arc source may also be used. LED light sources may also be used. The advantage of using LED light sources is that it will reduce the potential for the generation of uncomfortable heat, and therefore cause less discomfort to the subject. The irradiation of step (b) may be performed for the whole of the affected area. In particular, irradiation is performed for the whole interior of the mouth. For example, the light source may be manipulated such that accessible interior surfaces are irradiated. Alternatively, only some areas are irradiated. For example, individual pockets of areas may be irradiated. The light source may be adapted to irradiate all regions of the oral cavity, including under the tongue and through the flesh covered lingual, labial, anterior and posterior areas of the oral cavity and through the bite surface.

The light used in step (b) may have any suitable wavelength. The wavelength depends on the photosensitising compound used for the purposes of the present invention. For example, the wavelength of the light depends on the type of photosensitising compound's absorbance maxima. The wavelength of the light may range from the visible light range to the near infrared range of wavelength. The light source may have a wavelength ranging from about 400 nm to about 1400 nm. The light source may have a wavelength ranging from about 600 nm to about 900 nm. In particular, the wavelength is ranging from about 650 nm to about 800 nm. Even more in particular, the wavelength is about 660 nm, or about 664 nm. The irradiation enables the activation of the photosensitising compound. Accordingly, the wavelength used for the irradiation will depend on the photosensitising compound used for the PDT. For example, if indocyanine green (ICG) is used as the photosensitising compound, a laser light of 808 nm wavelength may be used. Further, near infrared light is expected to penetrate hard tissues better. It should be noted that any non-toxic photosensitiser, and subsequently light source with optimum wavelength, will be utilised to achieve light activation.

When endogenous pigments of obligatory anaerobes are used as 'endogenous photosensitisers' without the use of additional exogenous photosensitisers, light sources at a lower range in the visible spectrum is required. For example, if the endogenous pigment porphyrin in *Porphyromonas* is used as the photosensitiser in PDT, a light of wavelength of about 400 nm would be required.

The dose of light used in step (b) may range from 10 J/cm$^2$ to 200 J/cm$^2$. In particular, the dose of light may range from 50 J/cm$^2$ to 150 J/cm$^2$.

The intensity of the light source may range from 1 to 100 mW. In particular, the intensity may range from 20 to 50 mW. Even more in particular, the intensity of the light source is about 30 mW.

The irradiation of step (b) may be carried out for any suitable period of time. For example, the irradiation is carried out for a time period of about 30 minutes or less. For example, the irradiation of step (b) may be carried out for about 10 seconds to 30 minutes. The time period for carrying out the irradiation of step (b) may depend on the type of photosensitising compound used and the type of light used. In particular, the irradiation may be carried out for a time period of about 5 minutes to 15 minutes. Even more in particular, the irradiation is carried out for about 10 minutes. The irradiation may be performed for the entire mouth of the subject or specific regions of infection, for example, at the area of caries lesion or at the root canal.

The present invention also provides the cosmetic non-therapeutic method of the treatment, elimination or prevention of microorganisms in a subject, the method comprising the steps of:
(a) administering the photosensitising composition according to any aspect of the present invention; and
(b) irradiating the area to which the composition is administered with light at a wavelength absorbed by a photosensitising compound.

The method may be for treating and/or preventing conditions caused by microorganisms in the oral cavity of a subject. The subject may be an animal or a human.

Similarly to the other method and/or use described above, the photosensitising compound may be comprised in the photosensitising composition.

The treatment and/or prevention may further comprise a step of waiting a predetermined period of time between steps (a) and (b) above. The step of waiting for a predetermined period of time between steps (a) and (b) may be from about 1 minute to 5 days. The waiting step may be from about 10 minutes to 3 days. The waiting step may be from 20 minutes to 1 day. The waiting step may be from 30 minutes to 5 hours.

The steps described above may be repeated as often as required, for example until the condition has reduced to a desired level or has been eliminated. The steps may be repeated after intervals of predetermined periods. The interval for the repeatability of the steps would be obvious to a person skilled in the art. For example, the steps may be repeated every few hours, every day, every 2 or 3 days.

According to another aspect, the present invention provides a kit for treating and/or preventing conditions caused by microorganisms in a subject, the kit comprising the photosensitising composition according to any aspect of the present invention, disposed in at least one suitable container. The kit may be for treating and/or preventing conditions caused by microorganisms in the oral cavity of a subject. For example, the kit may be used for treating and/or preventing conditions caused by microorganisms, such as periodontal conditions and halitosis conditions. The conditions may include, but are not limited to, gingivitis, periodontitis dental caries, root caries, root canal infection, apical periodontitis and the like. The kit may also be used for elimination of bacterial biofilm in any localised infection and/or managing bacteria deep within dental caries lesions. In particular, the medicament may be used for elimination and inactivation of mature long-span biofilms. The subject may be an animal or a human.

At least one photosensitising compound may be comprised in the photosensitising composition in the kit. Alternatively, the at least one photosensitising compound may be disposed in a separate container or may be sold separately. The photosensitising compound may be any suitable photosensitising compound as described above. The kit may further comprise instructions on the use of the composition. The kit may also comprise at least one light emitting device capable of emitting light at a wavelength absorbed by the at least one photosensitising compound. The photosensitising compound may be an endogenous photosensitiser.

The present invention also provides a method of preparing the photosensitising composition described above. The method may comprise the step of: (a) preparing a mixture of at least one oxygen carrier, at least one oxidising agent and at least one surfactant. The at least one oxygen carrier, at least one oxidising agent and at least one surfactant may be as described above. In particular, the ratio of the volume of the at least one oxygen carrier to the at least one oxidising agent to the at least one surfactant in the mixture may be in the range of 50:40:10 to 80:19.8:0.2. The mixture of the at least one oxygen carrier, at least one oxidising agent, and at least one surfactant obtained in step (a) may be prepared by rigorously mixing the mixture formed. For example, the mixture may be prepared by sonicating or vortexing the at least one oxygen carrier, at least one oxidising agent, and at least one surfactant.

The method may comprise a further step of adding at least one photosensitising compound to the mixture of step (a). Any suitable photosensitising compound may be added, such as the ones described above.

The method may comprise a further step of adding at least one further surfactant; at least one alcohol; and/or water, wherein the ratio of the volume of the at least one further surfactant to the at least one alcohol to water is in the range of 10:5:85 to 40:30:30, with the proviso that when the at least one further surfactant is an alcohol, it is different from the at least one alcohol. The volume ratio may be in the range of 15:10:75 to 35:25:40. Even more in particular, the ratio is 30:20:50. In particular, the surfactant may be polyethylene glycol.

According to a particular aspect, the method may comprise a further step of adding a polyethylene glycol, an alcohol and water Any suitable alcohol may be used for the purposes of the present invention. For example, the alcohol may be a monohydric alcohol. The alcohol may also be a dihydric alcohol and/or a trihydric alcohol. A monohydric alcohol contains only one hydroxyl group in each molecule. Examples of monohydric alcohols include, but are not limited to, methanol, ethanol, propanol, butanol, pentanol, hexacecanoyl, melissyl alcohol and the like. Further, the monohydric alcohol may be a primary, secondary or tertiary alcohol. Examples of dihydric alcohols include glycols and diols. Examples of trihydric alcohols include glycerol. In particular, the alcohol is ethanol.

In particular, the method may comprise a further step of adding glycerol, ethanol and water. The ratio of the volume of glycerol to ethanol to water added to the mixture may be in the range of 10:5:85 to 40:30:30. In particular, the ratio may be in the range of 15:10:75 to 35:25:40. Even more in particular, the ratio is 30:20:50.

Having now generally described the invention, the same will be more readily understood through reference to the following examples which are provided by way of illustration, and are not intended to be limiting of the present invention.

EXAMPLES

Example 1

Materials

Unless otherwise stated, all chemicals and bacteriological media were purchased from Sigma-Aldrich Inc (St. Louis, Mo., USA). Methylene blue (MB) a phenothiazine photosensitiser dissolved in (a) water and (b) a mixture of glycerol:ethanol:water (30:20:50) was used. Diode laser (Model: PPM35 (LD1328) LDCU12-220, Power Technology Inc, Little Rock, Ark., USA) of wavelength 664 nm was used as the light source. The laser light from the source was coupled into a multimode fibre optic (400 μm outer diameter) delivery system with a bare fibre terminus. The maximum output energy at the bare fibre terminus was 30 mW.

Preparation of Tooth Specimens

The institutional review board of the National University of Singapore approved the collection and use of extracted human teeth for this experiment. Thirty single rooted teeth maintained in Phosphate Buffer Saline (PBS) with similar shape and sizes were selected for the following experiment. The crown (at the level of Cemento-Enamel Junction) and the apical two-third of the root were removed using a microslice machine (Metal Research, England) to obtain standard sized specimens of 8 mm length. The prepared tooth specimens were selected for the experiments after inspecting for any signs of cracks or damages on the cementum. The remnants of the pulp tissue were removed from the root canal using a barbed broach and the tooth specimens were autoclaved before further experiments.

Developing Bacterial Biofilm on Root Canal

A single colony of $E.$ $faecalis$ bacteria (ATCC 29212) culture was incubated in All Culture Broth (AC Broth) for 8 hours. The optical density of the culture was adjusted to 1 at 600 nm that corresponds to $10^9$ cells/mL. The sterilized tooth specimens were placed in the AC broth (50 mL) with the bacterial culture and incubated in an orbital incubator (120 rpm) at 37° C. under aerobic conditions. The culture medium was replenished once in every two days to remove dead cells and to ensure proper growth of bacteria. After four weeks of incubation, the tooth specimens were subjected to the following experiment.

Disinfection of Four-week Old Biofilm in Root Canal

This experiment was conducted to observe the efficiency of different antimicrobial treatments on a matured root canal biofilm. After the specific incubation period, the tooth specimens were removed and washed with sterile PBS. The specimens were randomly divided into five experimental groups and treated accordingly.

Group 1 (Control): Tooth specimens in this group were not subjected to any treatment (n=6).

Group 2 (conventional PDT): The tooth specimens in this group were subjected to conventional PDT. The root canals of the specimens were filled with 100 μM of MB (photosensitization) for 20 minutes and was irradiated immediately with 660 nm laser light for 20 minutes to attain a total energy level of 36 J (n=6). During irradiation, the bare fibre end of the multimode fibre optic cable coupled to the laser source was held still, immediately above the root canal orifice.

Group 3 (method of WO 2006/135344): Tooth specimens in this group were exposed to the method of photosensitising disclosed in WO 2006/135344. The root canals of the specimens were filled with 1 mM of MB in glycerol:ethanol:water (30:20:50) ("MIX") for 20 minutes towards photosensitization. The photosensitiser solution was subsequently replaced partially with perfluorodecahydro naphthalene and irradiated immediately with 660 nm laser light for 20 minutes to attain a total energy of 36 J (n=6). During irradiation, the bare fibre optic illumination tip was held still, immediately above the root canal orifice.

Group 4 (cleaning and shaping): The root canals of the tooth specimens in this group were subjected to conventional cleaning and shaping procedure (n=6). Conventional root canal instrumentation was carried out using a sequence of endodontic file sizes (#30 to #50 K-files; Maillefer Instruments SA, Ballaigues, Switzerland). To ensure standardisation, circumferential filing was used to shape the root canals. The canals were irrigated with 5 mL of 5.2% sodium hypochlorite before instrumentation, in-between each file change and as the last irrigant using a 28-gauge needle and syringe. Ethylenediaminetetraacetic acid (EDTA) of concentration of 17% in water was used at the end of the instrumentation to remove the smear layer.

Group 5 (method of WO 2006/135344 combined with cleaning and shaping): Tooth blocks in this group were subjected to disinfection by both endodontic cleaning (chemicals) and shaping (instrumentation) and the method disclosed in WO 2006/135344 (n=6). The methodology for endodontic cleaning and shaping was similar to Group 4, while the steps for the method of WO 2006/135344 were similar to Group 3.

After the specific treatment procedures, the tooth specimens in all the groups were sectioned longitudinally into two equal halves. The dentine shavings from the root canal surface on the mid portion of the sections were collected using a long shank round bur of size 3. The collected dentinal shavings were enriched for bacterial growth and were plated to enumerate the bacterial colony forming units (CFU). In particular, the dentine shavings were mixed with sterile AC broth and incubated at 37° C. for five hours to enrich the number of surviving bacteria. He bacterial suspensions were later serial diluted (10 fold) and 100 μL of each dilution was plated on AC Agar plates to enumerate the CFU after 12 hours incubation at 37° C. All the above mentioned procedures were conducted in a biosafety cabinet to avoid contamination.

Statistical Analysis

All experiments were repeated three times in triplicate and the statistical significances were analyzed by two-way analysis of variance (ANOVA). Any p values less than 0.05 was considered significant.

Results

Disinfection of Four-week Old Biofilm in Root Canal

FIG. 1 shows the $\log_{10}$ number of bacterial cells surviving different antimicrobial treatment on 'matured' four-week old $E.$ $faecalis$ biofilms. Complete inactivation of bacteria was not seen with any of the treatment groups. Bacterial survival after the treatment was in the order: control>PDT>Method of WO 2006/135344 >cleaning and shaping>cleaning+shaping combined with the method of WO 2006/135344. Compared to group 2, group 3 produced marked reduction in the bacterial count (approximately 1.5 $\log_{10}$ difference that corresponded to 96.7% bacterial kill). Endodontic cleaning and shaping produced a difference of about 3.27 $\log_{10}$ in viable biofilm bacterial cells (99.96% bacterial kill), while group 5 produced 7.02 $\log_{10}$ difference in the bacterial count compared to control group (99.99% bacterial kill). When different treatment groups were compared, it was noted that the elimination of bacteria was significantly high when conventional endodontic cleaning and shaping was combined with the method of WO 2006/135344 (P<0.05).Group 2 with direct irradiation of MB in water failed to show significant bacterial reduction (a difference of 0.38 $\log_{10}$ that corresponds to a 59% bacterial kill).

Discussion

The results show that there is greater resistance of matured 4-week old biofilm bacteria to all tested disinfection methods. The results from Group 3 showed considerable bacterial inactivation (96.7%) when compared to Group 2. The resistance of 'matured' biofilm bacteria to chemical disinfectants and photosensitisers warrants the use of a photosensitising composition that can diffuse well into the biofilm matrix, yields high levels of singlet oxygen and larger fluence (laser energy per unit area) of light. In conclusion, it can be seen that even the photosensitising composition and photosensitising method disclosed in WO 2006/135344 is not effective in eliminating mature long-span biofilm.

Example 2

Materials

Unless otherwise stated, all chemicals and bacteriological media were purchased from Sigma-Aldrich Inc (St. Louis, Mo., USA). Methylene blue (MB), a phenothiazine dye, was used as the photosensitiser; perfluorodecahydro naphthalene was used as the oxygen carrier; hydrogen peroxide ($H_2O_2$) (Cica Reagents, Japan) was used as the oxidising agent; and a non-ionic detergent, triton-X100 (Bio-Rad-Laboratories, USA) was used as the surfactant. A diode laser of wavelength 664 nm (wavelength for MB excitation) with output energy of 30 mW was used as the light source. The laser light was delivered using an optical fiber of a 400 μm outer diameter (Power Technology Inc, Little Rock, Ark., USA).

Chemical Assays

Four different photosensitising compositions were tested for model substrate oxidation and singlet-oxygen generation. The formulations were as shown in Table 1.

TABLE 1

Compositions of different photosensitising compositions

| Formulation | Composition |
| --- | --- |
| PF1 | 50 μM of MB in combination with perfluorodecahydro naphthalene |
| PF2 | 50 μM of MB in combination with perfluorodecahydro naphthalene and $H_2O_2$ (volume ratio = 66.6:33.3) |
| PF3 | 50 μM of MB in an emulsion produced by mixing perfluorodecahydro naphthalene:$H_2O_2$:triton-X100 in the ratio 60:35:5 |
| PF4 | 50 μM of MB in an emulsion produced by mixing perfluorodecahydro naphthalene:$H_2O_2$:triton-X100 in the ratio 75:24.5:0.5 |

The photooxidizing activity of the different photosensitizing formulations was evaluated by fluorimetrically measuring the photooxidation of model substrate N-acetyl-L-tryptophanamide (NATA). MB, at a final concentration of 50 μM in the different formulations containing 10 μM NATA was taken in a fluorimetric cuvette. The test solution was irradiated with 664 nm in order to induce the generation of oxidizing agents. The rate of decrease of NATA concentration with an increasing dose of irradiation was recorded by measuring the intensity of 290 nm excited fluorescence emission spectrum at 300-400 nm typical of the tryptophanyl moiety of NATA.

Singlet-oxygen generation was assessed photometrically using 1,3-diphenylisobenzofuran (DPBF), a singlet-oxygen scavenger. DPBF at a concentration of 100 μM that corresponds to an absorbance between 1.5 and 2 at 420 nm was mixed with 10 μM MB in different test formulations (total volume 3 mL). The rate of singlet-oxygen production was related to the rate of decrease in DPBF concentration (calculated from the absorbance at 420 nm using UV-VISIBLE Spectrophotometer, Shimadzu, Japan) as a function of the irradiation dose. All experiments were repeated in triplicate, and the statistical significances of mean value were analyzed by one-way analysis of variance, and p values less than 0.05 were considered significant.

Antibiofilm Efficacy (i) Characterisation of Structural Damage to Biofilm by PDT: In vitro The structural damage to biofilm caused by PDT was assessed on E. faecalis biofilms grown on a glass cover slip that was fixed covering a grove (6 mm diameter) made at the bottom part of a petri dish. E. faecalis cell suspension (100 μL containing ~$10^7$ cells/mL) prepared from overnight grown culture in All-Culture (AC) media was added onto the saliva-coated glass-cover slip. Six petri dishes containing the biofilm were tested in each group. After seven days of incubation with periodical replacement of growth media, the biofilm was washed and photosensitised with either 100 μM MB in water or PF4 (MB in an emulsion produced by mixing perfluorodecahydro naphthalene:$H_2O_2$:triton-X100 in the ratio 75:24.5:0.5). These biofilms were incubated in the dark for ten minutes, after which the excess of the photosensitising formulation was partially replaced with perfluorodecahydro naphthalene and exposed to irradiation using 664 nm diode laser with a total fluence of 31.84 J/cm².

After the PDT, the washed biofilms were stained using 20 μL PBS containing 2 μL of live/dead stain (Molecular Probes, Eugene, Oreg., USA) and were observed using confocal laser scanning microscopy (CLSM). Confocal illumination was provided by a Kr/Ar laser (488 nm laser excitation) fitted with a long-pass 514 nm emission filter. Nine windows from each sample were imaged using 60× water-immersion lenses. The optical sections of the biofilm structure were recorded and analyzed by using FluoView software (Olympus Corporation, Tokyo, Japan).

(ii) PDT of Endodontic Bacterial Biofilm: Ex Vivo

The institutional review board of the National University of Singapore approved the collection and use of extracted human single-rooted anterior teeth (from young adults ages 16 to 24 years) for this experiment.

Thirty tooth blocks were prepared by removing the crown at the level of cementoenamel junction and the apical third of the root canal (~8 mm long). All specimens were instrumented using K-files with sizes from #20 to #40. The smear layer formed during mechanical shaping was removed by rinsing the root canal with sodium hypochlorite (1%) followed by EDTA (100 mM). The prepared single-rooted tooth specimens were incubated with 50 mL of AC media inoculated with a single colony of E. faecalis as described elsewhere (George S and Kishen A, J Biomed Opt, 2000). Incubation was carried out for ten weeks at 37° C. with periodical replacement of growth media under constant shaking (120 rpm). After the incubation period, the tooth specimens were randomly divided into five groups and were treated as follows:

Group 1—Control group (n=5): root canals were not subjected to any treatment.

Group 2—Root canal-treatment (RCT) group (n=5): root canals were subjected to conventional cleaning and shaping procedures performed by using a sequence of endodontic file sizes (#25 to #50 K-files; Maillefer Instruments SA, Switzerland). The root canals were repeatedly irrigated with 5 mL of 5.2% sodium hypochlorite before and after instrumentation step using a 28-G needle and a syringe. Ethylenediaminetetraacetic acid (EDTA) 17% was also used at the end of instrumentation to remove the smear layer.

Group 3—Conventional PDT group (n=5): root canals were subjected to minimal instrumentation (using #25 K file). These root canals were filled with 100 μM MB in water and were irradiated with 664 nm laser light with a total energy of 31.84 J/cm².

Group 4—PF4 group (n=5): root canals were subjected to minimal instrumentation (using #25 K file) followed by PDT using PF4. Here, the root canals were filled with PF4 and were left in the dark for 10 minutes. After the sensitization period, the excess of the photosensitizing formulation was partially replaced with perfluorodecahydro naphthalene and the root canals were irradiated with 664 nm diode laser with a total fluence of 31.84 J/cm$^2$.

Group 5—RCT+PF4 group (n=5): root canals were subjected to the conventional root canal disinfection procedure similar to the conventional RCT group (i.e. Group 2) followed by PDT using PF4.

After the specified treatment, the tooth-specimens were split open mesiodistally, and dentine shavings were collected using a round bur of 1 mm diameter held perpendicular to the root canal surface. The dentine shavings were collected at midpoint (coronoapically) from the two halves (buccal and lingual) of each root (n=12). These shavings were inoculated into 1 mL of fresh AC medium and were incubated at 37° C. for 4 hours to enrich the number of bacteria. Serially diluted samples (100 µL) were plated on AC agar as triplicate. Colony-forming units (CFU) were enumerated on the subsequent day, and the mean value of $\log_{10}$ number of bacteria and the standard error were calculated. Because the extreme low level of bacterial cells (<100 cells/mL) in the initial inoculums may fail to show CFU after 4 hours of enrichment, the bacteriologic status of the dentine powders suspended in growth media were assayed after 24 hours of incubation. The numbers of tubes positive for bacterial cells were counted against the total number of tubes.

Results (i) Chemical Assays

Figure 2A:
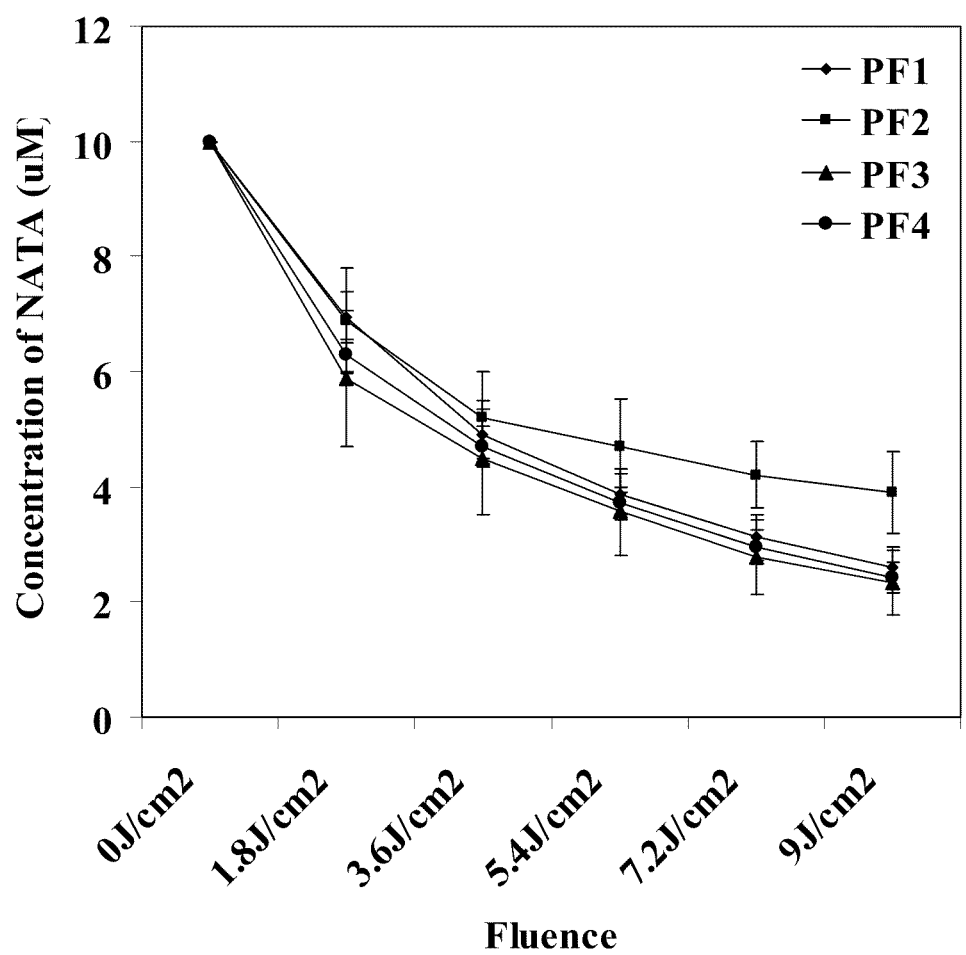
FIG. 2A shows the oxidation of NATA caused by oxygen based-free radicals measured as the reduction of NATA concentration.
Figure 2B:
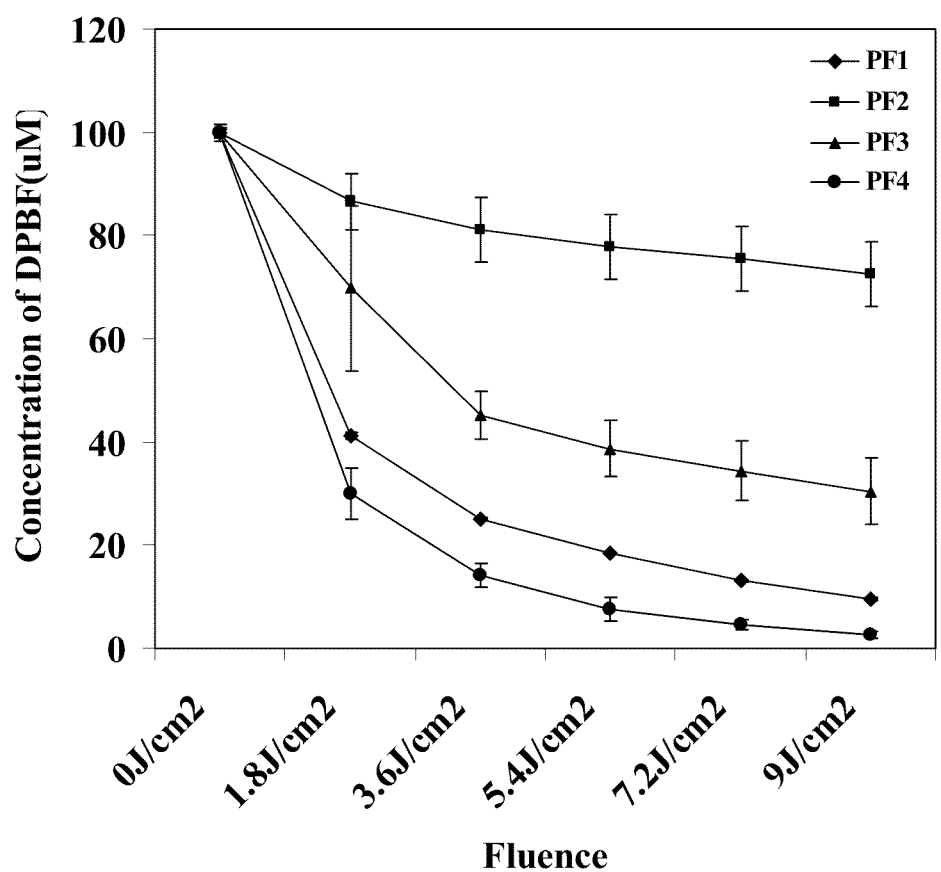
FIG. 2B shows the oxidation of DPBF indicating the singlet-oxygen generation during irradiation of different photosensitising compositions.

The time-depended reduction in fluorescence intensity at 360 nm because of the photooxidation of NATA is given in FIG. 2A. PDT using PF1 showed significantly reduced NATA oxidation rate (1.21 µM/minute) compared with other photosensitising formulations (p<0.05). The rate of DPBF bleaching indicative of singlet-oxygen generation was influenced by the photosensitising formulation used and was significantly different for each test formulations (p<0.001) (FIG. 2B). The ability to produce singlet-oxygen in different photosensitising formulations was in the order PF4>PF1>PF3>PF2 that corresponded to a rate of 1.95 µM/min, 1.8 µM/min, 1.39 µM/min and 0.55 µM/min, respectively.

(ii) Characterisation of Structural Damage to Biofilm by PDT: In Vitro

Figure 3:
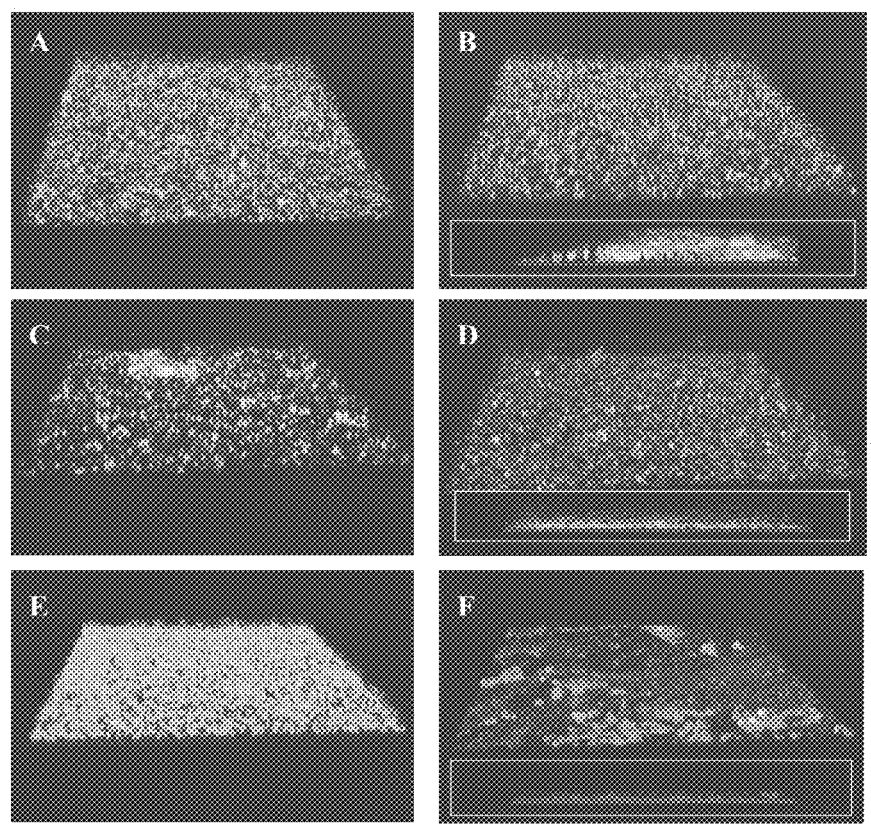
FIG. 3 shows the three dimensional confocal laser scanning microscopy reconstruction of the biofilm subjected to PDT (inlet shows the saggital section) (60×). (A) The biofilm receiving no treatment, (B) the biofilm subjected to irradiation alone, (C) the biofilm subjected to sensitization with 100 μM MB, (D) the biofilm subjected to sensitisation with MB followed by irradiation, (E) the biofilm subjected to PF4, (F) the biofilm subjected to PF4 and irradiation.

CLSM analyses of biofilms before and after being subjected to PDT are shown in FIG. 3. FIG. 3A shows the biofilm that was neither subjected to sensitization nor to light irradiation. This biofilm was continuous without marked variation in the thickness (17 µm). As evident from FIG. 3B the viability status of bacteria in the biofilm was not affected by irradiation alone and the thickness of the biofilm was unchanged. Biofilm subjected to PDT using MB dissolved in water increased the proportion of dead cells (FIG. 3D) and the biofilm thickness was 12 µm, which was lower than the control (FIG. 3C). However, the treatment was not sufficient to cause a major destruction of biofilm structure or inactivation of biofilm bacteria. Biofilms exposed to PDT using PF4 is shown in FIG. 3F. A large proportion of the bacteria in the biofilm were killed under this condition. Most importantly, the remnant of biofilm was thinner (6 µm) and discontinuous, indicating marked disruption of the biofilm structure.

(iii) PDT of Endodontic Bacterial Biofilm: Ex Vivo

The results of different antibacterial treatment on endodontic biofilm are presented in Table 2. Significant decreases in the viability of *E. faecalis* biofilms were observed under all the treatment conditions when viable bacterial cells were enumerated after 4 hours of enrichment. When the biofilm was subjected to PDT using MB dissolved in water, there was a difference of 1.5 $\log_{10}$ in the mean viable count that corresponded to 96.89% reduction in viable bacteria compared with the control group. Complete killing of bacteria was observed when the root canals were subjected to RCT, PDT using PF4, and the treatment comprising RCT combined with PDT using PF4. However, bacteriological evaluation of dentine shaving after 24 hours of enrichment showed all the groups except PF4 and RCT+PF4 groups positive for bacterial growth. Although none of the tubes from conventional RCT group showed bacterial presence when plated after 4 hours of enrichment, 60% of the specimens showed bacterial growth after 24 hours of enrichment. The results overall showed that unlike RCT that may reduce the number of viable bacteria in an endodontic biofilm, PDT using PF4 can ensure more complete eradication of endodontic bacterial biofilm.

TABLE 2

The efficacy of different endodontic disinfection techniques tested in the ex vivo study

| Treatment group | CFU ($\log_{10}$) after 4 hours of enrichments (±SD) | % of tooth specimens positive for bacteria after 24 hours of enrichment |
|---|---|---|
| 1 | 7.147 (±0.601) | 100 |
| 3 | 5.639 (±0.066) | 100 |
| 2 | 0.0 | 60 |
| 4 | 0.0 | 0 |
| 5 | 0.0 | 0 |

Discussion

Model substrate oxidation experiments showed enhanced photooxidation and singlet oxygen generation when oxygen carrier-oxidizing agent emulsion was used in the photosensitising composition. These results highlighted that during irradiation of oxygen carrier-oxidizing agent emulsion, reactive oxygen species (ROS) other than singlet oxygen were also generated. This reaction, which may happen in the absence of molecular oxygen, is important in eradicating bacterial growth under reduced oxygen tension as in the case of many in vivo environments including endodontic infection.

Earlier CLSM observations of matured biofilm have shown the formation of pockets of viable bacterial cells inside the mineralized matrix of matured biofilm (Jefferson K K, 2004). The present example shows that PDT using PF4 could breakdown the biofilm matrix and inactivate bacteria as evident from the reduced thickness and the discontinuity in biofilm structure (FIG. 3). The superior bactericidal action could be is as a result of the complementing function of oxygen carrier that ensures adequate concentration of oxygen and oxidizing agent that degrade the biofilm matrix, thus facilitating the penetration of photosensitiser into the biofilm. The increased photooxidation potential and singlet-oxygen generation collectively contributed toward the biofilm matrix disruption and bacterial inactivation during PDT using PF4.

It is evident from this study that 'matured' endodontic bacterial biofilm can be effectively inactivated by PDT using PF4. Although conventional endodontic disinfection procedure showed no viable bacteria after 4 hours of the enrichment process, 60% of the root canal shavings confirmed bacterial growth after 24 hours of incubation. This observation suggested the possibility of bacterial re-growth after disinfection. However, PDT using PF4 alone or in combination with conventional disinfection technique showed the absence of bacteria even after 24 hours of incubation, suggesting complete bacterial inactivation. The chemical assays used in this study showed no obvious difference in the photooxidation potential of PF4 compared with other photosensitising compositions. However, compared to other compositions, PF4 produced significantly increased rate of singlet oxygen generation. This increased singlet oxygen generation may be responsible for more complete inactivation and disruption of matured biofilm observed in this study. In conclusion, 'matured' bacterial biofilm that is generally resistant to antimicrobial agents, can be disrupted and inactivated by using a photosensitising composition comprising an emulsion of oxygen-carrier, oxygen carrier and surfactant, which may further comprise a photosensitiser.

Example 3

The photosensitising composition of the present invention was analysed for the production of antibacterial reactive oxygen species using chemical assays and antibacterial property on biofilm of *Enterococcus faecalis*. Photosensitising composition comprising 100 µM MB was prepared in four different formulations. Two of these formulations were emulsions prepared by mixing different proportions of an oxygen carrier solution (perfluorodecahydro naphthalene), oxidizing agent ($H_2O_2$) and surfactant (tween X100). The mixture of oxygen carrier, oxidizing agent and oxygen carrier alone were also subjected to different analysis.

Chemical Assays

All the chemicals used in the study were of analytical grade and were purchased from Sigma Aldrich, St. Louis, Mo., USA, unless otherwise mentioned. Methylene blue (MB), a phenothiazine dye, was used as the photosensitiser. Four different photosensitising compositions were tested in this study.

ET2: Emulsion produced by mixing perfluorodecahydro naphthalene:$H_2O_2$:tween X100 in the ratio 60:35:5;

ET6: Perfluorodecahydro naphthalene:$H_2O_2$:tween X100 in the ratio 75:24.5:0.5;

Sol A+B: Perfluorodecahydro naphthalene and $H_2O_2$ (66.6: 33.3); and

Sol A: Perfluorodecahydro naphthalene alone.

Glycerol and ethanol are widely used as vehicle for various pharmaceutical and commercial products such as drugs, cosmetics and foods. The multi-component formulation of glycerol:ethanol:water in a volume ratio of 30:20:50 ("MIX") is expected to facilitate the photosensitiser diffusion into dentinal tubules and anatomical complexities of root canal. It has been shown that the given ratio of glycerol:ethanol:water to be optimum with regard to photosensitiser uptake by bacterial cells and bactericidal action upon irradiation. Accordingly, the MB was dissolved in MIX to form a photosensitiser solution.

Diode laser of wavelength 664 nm (wavelength for MB excitation) with output energy of 30 mW was used as the light source. The laser light was delivered using an optical fibre of 400 µm outer diameter (LDCU/6130, Power Technology Inc, Little Rock, Ark., USA).

(i) NATA Oxidation

The photooxidising activity of MB (in different photosensitising compositions) was evaluated by fluorimetrically measuring the photooxidation of model substrate N-acetyl-L-tryptophanamide (NATA). NATA is a widely accepted model molecule to test the oxidation potential of photosensitizing agents. Oxidation of NATA can be caused by type 1 or type 2 mechanism of photosensitization. MB (50 µM) in tested formulations containing 10 µM NATA was taken in a fluorimetric cuvette (10×10 mm) and the fibre tip was kept as close as possible to the liquid surface without touching. Irradiation was carried out with 664 nm diode laser of power 30 mW. The test solution was maintained undisturbed during the experiment. The rate of decrease of NATA concentration along the increasing time of irradiation (1 minute intervals for 5 minutes) was followed by measuring the intensity of 290 nm-excited fluorescence emission spectrum (300-400 nm) typical of the tryptophanyl moiety of NATA.

(ii) Singlet Oxygen Measurement

Singlet oxygen measurements were carried out in a quartz cuvette (10×10 mm) according to a procedure described in literature (George S and Kishen A, J Biomed Opt, 2007).

The assessment of different photosensitising compositions comprising MB generating singlet oxygen upon irradiation was studied photometrically using 1,3-diphenylisobenzofuran (DPBF), a singlet oxygen scavenger. DPBF (100 µM) corresponding to absorbance between 1.5 and 2 at 420 nm was mixed with 10 µM MB in different formulations (total volume 3 mL). The experiment was performed as in (i) NATA above without dipping the fibre tip into solution. The decrease in absorbance intensity at 420 nm was monitored for an irradiation period of 5 minutes (at 1 minute intervals) using UV-VISIBLE Spectrophotometer (Shimadzu, Japan). The rate of singlet oxygen production was related to the rate of decrease of DPBF absorbance at 420 nm as a function of irradiation time.

Bactericidal Action of Modified PDT on Biofilm Bacteria (i) PDT on Bacterial Biofilms Grown in Multiwall Plates Four days old biofilms of *E. faecalis* was produced in wells of multiwell plates (material: polystyrene) using All Culture (AC) medium. After the incubation period, the growth media was removed and wells were rinsed with deionized water, retaining the biofilm bacteria in the well. Biofilm growth was evident on the walls of the wells upon visual examination. The biofilm bacteria formed on wall of multiwell plates was sensitized with 100 µM MB in the different photosensitising compositions for 10 minutes. The volume of photosensitising composition used was same as the original volume of growth media (100 µL), to cover the biofilm produced in the well.

The wells were irradiated for 10 minutes with the same light source used for the chemical assays of this example. During irradiation the tip of the optical fibre was placed just above the irradiating media and the plate was shaken using a plate shaker. The total energy delivered from the tip of the optical fibre was 18 Joules. After treatment, the liquid in the wells was replaced with fresh growth media and vigorously shaken. Growth media was flushed using a micropipette for mechanically disrupting the biofilm bacteria on the walls of the wells. Serial dilutions were carried out in the growth medium, and 100 µL from each dilution was spread plated on to AC agar to enumerate the surviving bacterial cells.

(ii) PDT on Bacterial Biofilms Grown in Tooth Specimens

Since ET6 showed better result in eradicating biofilm bacteria from multiwell plate (FIG. 6), its efficiency in eradicating 'matured' biofilm formed on root canal wall of tooth was tested in this stage. In addition, the antibacterial effectiveness of other conventional treatment strategies such as root canal treatment (RCT) and conventional PDT approach were also compared at this stage. This would enable us to assess the suitability of using photosensitising composition ET6 in treating endodontic infections involving biofilms.

Thirty single rooted non-carious teeth were collected. They were prepared by removing the crown at the level of cemento-enamel junction, and the apical third of the root to obtain a standard length of 8 mm. In order to minimize variation in the internal dimensions of root canal and for standardization, all specimens were instrumented using K files with sizes from #20 to #40. The smear layer formed during mechanical shaping was removed by rinsing of root canal with sodium hypochlorite (1%) followed by EDTA (100 mM). Washed tooth specimens were incubated with 50 mL of AC media inoculated with a single colony of *E. faecalis*. Incubation at 37° C. for ten weeks was done with constant shaking at 120 rpm. The growth medium was replaced with fresh media every four days.

After the incubation period, the tooth specimens were randomly divided into five groups and treated accordingly. The groups were as follows:

Control group (n=5): Tooth specimens in this group were not subjected to any treatment Conventional RCT (n=5): Tooth specimens in this group were subjected to conventional root canal therapy Conventional PDT (n=5): Tooth specimens in this group were subjected to minimal instrumentation followed by conventional PDT, where the root canal was filled with 100 μM of MB and irradiated with a total energy of 36 Joules.

ET6 group (n=5): Tooth specimens in this group were subjected to minimal instrumentation followed by PDT using ET6 photosensitising composition.

RCT-ET6 group (n=5): Tooth specimens in this group were subjected to conventional root canal therapy followed PDT using ET6 photosensitising composition.

After the specified treatment, the tooth blocks were cut open and dentine shavings were collected from two spots at the root canal wall. The first dentinal shavings were taken 2 mm away from the point of irradiation. The dentine shavings were inoculated in 1 mL of fresh AC medium and were incubated for 24 hours. Long duration of incubation was provided so that even lesser number of surviving bacteria can grow. After the incubation period, serial dilutions were made and 100 μL was plated on AC agar. Enumeration of CFU was performed the subsequent day.

Results (i) NATA Oxidation

Figure 4:
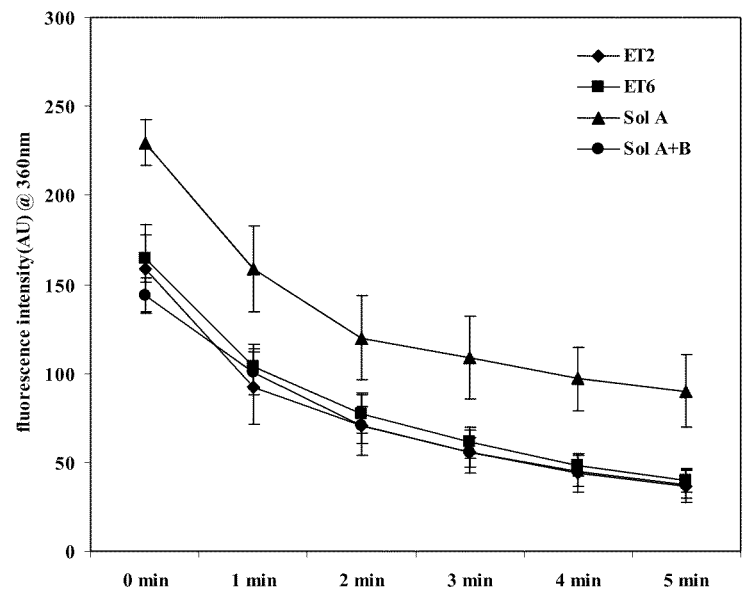
FIG. 4 shows the oxidation of NATA caused by oxygen based free radicals measured as drop in fluorescence intensity at 360 nm.

Under the experimental conditions, the NATA oxidation caused by PDT was found to follow a $1^{st}$ order kinetics (FIG. 4). The rate of NATA oxidation when PDT was conducted using ET6, ET2 and Sol A+B showed a similar trend. However, PDT using photosensitising composition containing perfluorodecahydro naphthalene alone (i.e. Sol A) showed significantly reduced NATA oxidation rate compared to other the photosensitising compositions.

(ii) Singlet Oxygen Yield

Figure 5:
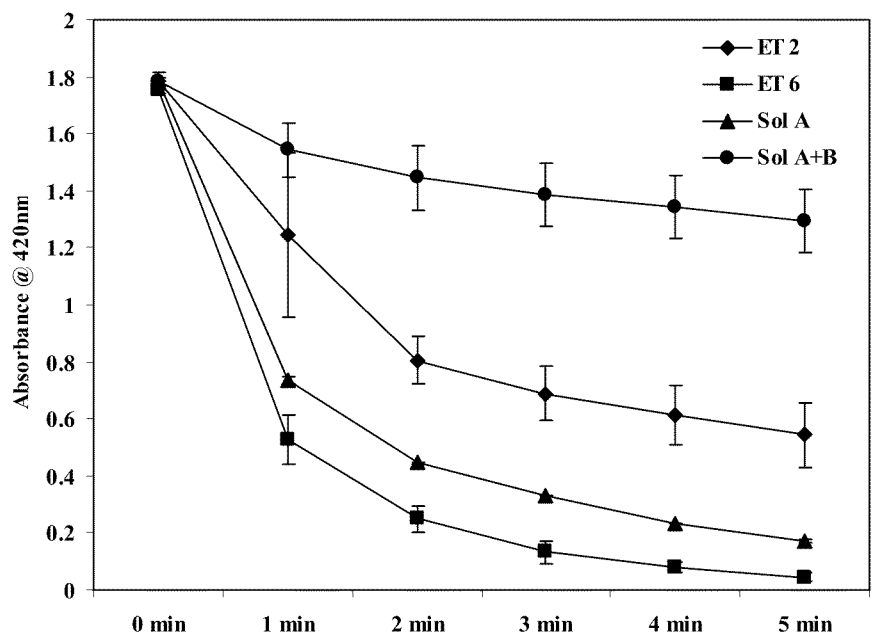
FIG. 5 shows the oxidation of DPBF indicating the singlet oxygen generation during irradiation of different photosensitising compositions.

The raw kinetic data in the form of decrease in absorbance value at 420 nm as a function of time in minutes is shown in FIG. 5. The ability to produce DPBF bleaching species (singlet oxygen) in different photosensitising compositions was in the order ET6>Sol A>ET2>SoIA+B.

(iii) PDT on Biofilm Grown in Multiwall Plates

Figure 6:
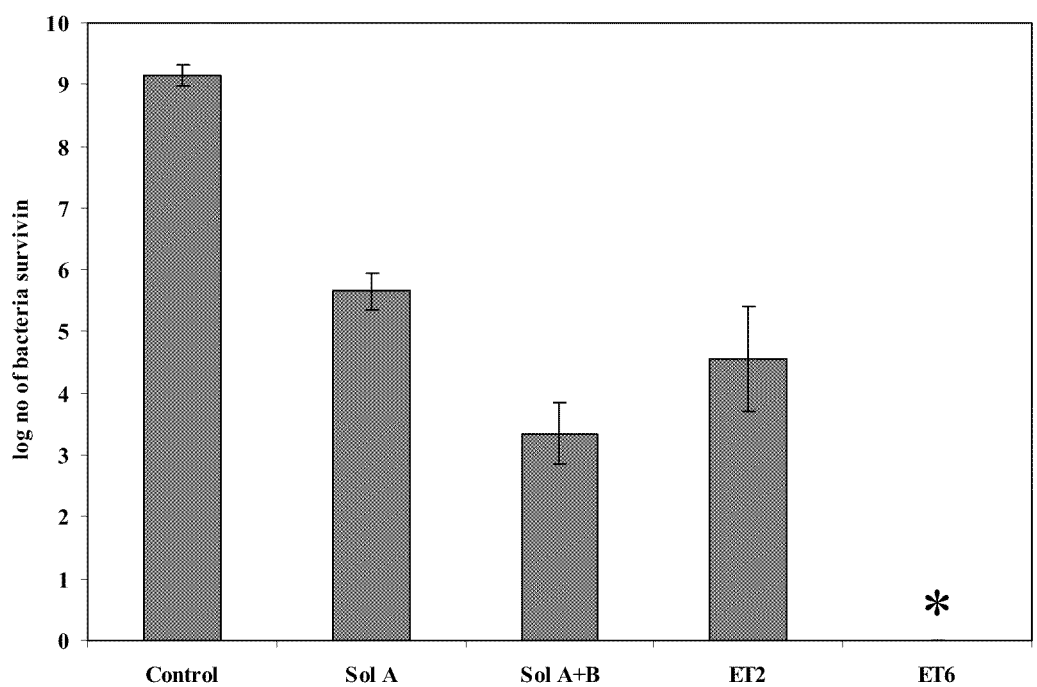
FIG. 6 shows the log number of bacteria surviving the photodynamic therapy using different photosensitising compositions.

FIG. 6 shows the $log_{10}$ number of *E. faecalis* surviving after the PDT treatment. Compared to the control group, all the other photosensitising compositions showed significant reduction in the bacterial count. However, PDT performed with ET6 as the photosensitising composition alone showed 100% bacterial eradication.

(iv) PDT on Bacterial Biofilms Grown in Tooth Specimens

Figure 7:
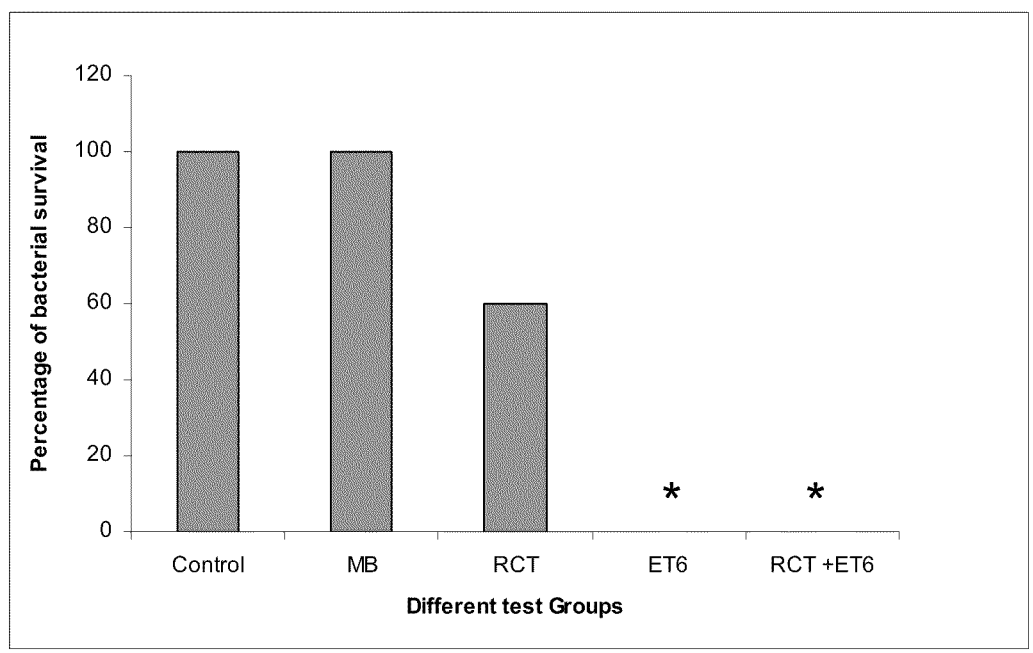
FIG. 7 shows the percentage of surviving bacteria after root canal treatment with different treatments.

The bacteriological status of tubes added with dentine shavings were analyzed after 24 hours of incubation at room temperature. All the treatments except the treatment using ET6 alone as the photosensitising composition and the treatment which combined conventional RCT with PDT using ET6 as the photosensitising composition showed bacterial growth (FIG. 7). This result confirmed that PDT involving the use of ET6 as a photosensitising composition can ensure complete elimination of bacteria from root canal biofilm. Although none of the tubes from conventional RCT group showed bacterial presence when plated after 4 hours of incubation, 60% showed bacterial growth after 24 hours. The data suggested that, although RCT may reduce the number of viable cells, it may not completely eliminate the bacteria from root canal biofilm.

REFERENCES

1. WO 2006/135344
2. Economou-Stamatelopoulou C et al, Apostolopoulos M. OPHTHALMOLOGICA 217 (6): 426-430 November-December 2003
3. Dougherty W J et al, Journal of Endodontics, 24(5):356-8, 1998
4. Detty M R et al, J Med Chem, 47(16):3897-915, 2004
5. George S and Kishen A, Journal of Biomedical Optics, 12(3):034029, 2007
6. George S and Kishen A, Journal of Endodontics, 33(5): 599-602, 2007
7. J D Whitney, Heart and Lung, 1989, 18, page 466. General information about high pressure oxygen in wound healing
8. Jefferson K K., FEMS Microbiol Lett, 236(2):163-173, 2004
9. Kishen A et al, Journal of Biomed Mater Res A., 77(2): 406-15, 2006
10. Pervaiz S, Faseb Journal, 2001, 15(3):612-617
11. Soncin M et al, Photochem. Photobiol. Sci., 1:815-819, 2002
12. Soukos N S et al, Antimicrobial Agents and Chemotherapy, 42(10):2595-2601, 1998
13. Yoshida H et al., Applied Optics, 36(16), pp 3739-3744, 1997

The invention claimed is:

1. A photosensitising composition for photodynamic elimination of a mature long-span bacterial biofilm of a root canal, the photosensitising composition comprising a liquid mixture of:
   at least one photosensitising compound;
   at least one oxygen carrier selected from the group consisting of perfluorodecalin, perfluorohexane, and mixture thereof;
   at least one oxidizing agent selected from the group consisting of: hydrogen peroxide, dilute sodium hypochlorite, DMSO and chlorine dioxide;
   non-ionic detergent;
   at least one surfactant selected from the group consisting of: glycerol, polyethylene glycol, and mixture thereof;
   at least one alcohol selected from the group consisting of methanol, ethanol, propanol, butanol, pentanol, and melissyl alcohol; and
   water;
   wherein the ratio of the volume of the at least one oxygen carrier to the at least one oxidizing agent to the non-ionic detergent is in a range of 60:39:1 to 76:23.6:0.4;

wherein the at least one alcohol includes ethanol such that a ratio of the volume of the at least one surfactant to ethanol to water is 30:20:50; and wherein the photosensitising composition is configured to degrade the mature biofilm matrix and to penetrate into the biofilm of the root canal.

2. The photosensitising composition according to claim 1, wherein the ratio of the volume of the at least one oxygen carrier to the at least one oxidizing agent to the non-ionic detergent is 75:24.5:0.5.

3. The composition according to claim 1, wherein the composition further comprises a pharmaceutically acceptable excipient and/or carrier.

4. The composition according to claim 1, wherein the composition is formulated: as an oral rinse, mouthwash, and/or atomizing spray; for topical administration; or for administration by injection.

5. The photosensitising composition of claim 1, wherein the at least one photosensitising compound is a phenothiazine dye.

6. The photosensitising composition of claim 1, wherein the at least one photosensitising compound is selected from the group consisting of toluidine blue, methylene blue, arianor steel blue, tryptan blue, crystal violet, azure blue cert, azure B chloride, azure II, azure A chloride, azure B tetrafluoroborate, thionin, azure A eosinate, azure B eosinate, azure mix sicc., azure II eosinate, haematoporphyrin HCI, haematoporphyrin ester, aluminium disulphonated phthalocyanine, chlorins, photoactive fullerenes, aminolevulinic acid (ALA), bacteriochlorins, phthalocyanines, pheophorbides, purpurins, naphthalocyanines, indocyanine green, and mixtures thereof.

7. A method of treating a root canal in a subject in need of treatment, wherein the method comprises the steps of:
   a) administering the photosensitising composition according to claim 1 to the root canal of the subject; and
   b) irradiating an area to which the composition is administered with light at a wavelength absorbed by the at least one photosensitising compound.

8. The method according to claim 7, wherein the composition in step a) is administered topically or by injection.

9. A method of preparing the photosensitising composition according to claim 1, comprising the steps of
   a) mixing (1) at least one oxygen carrier selected from the group consisting of perfluorodecalin, perfluorohexane, and mixture thereof, (2) at least one oxidizing agent selected from the group consisting of hydrogen peroxide, dilute sodium hypochlorite, DMSO and chlorine dioxide, and (3) non-ionic detergent to prepare a mixture;
   b) adding to said mixture (4) at least one photosensitising compound, (5) at least one surfactant selected from the group consisting of glycerol, polyethylene glycol, and mixture thereof, (6) at least one alcohol selected from the group consisting of methanol, ethanol, propanol, butanol, pentanol, and melissyl alcohol, and (7) water to obtain a liquid mixture which is the photosensitising composition;
   wherein the ratio of the volume of the at least one oxygen carrier to the at least one oxidizing agent to the non-ionic detergent is in a range of 60:39:1 to 76:23.6:0.4;

wherein the at least one alcohol includes ethanol;

wherein the ratio of the volume of the at least one surfactant to ethanol to water is 30:20:50; and wherein the photosensitising composition is configured to degrade mature biofilm matrix and to penetrate into the biofilm of root canal.

10. The method according to claim 9, wherein the mixture obtained in step a) is prepared by sonicating or vortexing the at least one oxygen carrier, at least one oxidizing agent, and non-ionic detergent.

11. The method according to claim 9, wherein the at least one surfactant is polyethylene glycol and at least one alcohol is ethanol.

12. The method according to claim 11, wherein the ratio of the volume of the polyethylene glycol to ethanol to water is 30:20:50.

13. A photosensitising composition for photodynamic elimination of a mature long-span bacterial biofilm of a root canal, the photosensitising composition comprising a liquid mixture consisting essentially of:
   at least one oxygen carrier selected from the group consisting of perfluorodecalin, perfluorohexane, and mixture thereof;
   at least one oxidizing agent selected from the group consisting of: hydrogen peroxide, dilute sodium hypochlorite, DMSO and chlorine dioxide;
   non-ionic detergent;
   at least one surfactant selected from the group consisting of: glycerol, polyethylene glycol, and mixture thereof;
   at least one alcohol;
   water; and
   at least one photosensitising compound;
   wherein the ratio of the volume of the at least one oxygen carrier to the at least one oxidizing agent to the non-ionic detergent is in a range of 60:39:1 to 76:23.6:0.4; and
   wherein the photosensitising composition is capable of producing increased rate of singlet oxygen generation and photooxidation for a complete inactivation and disruption of the matured long-span bacterial biofilm.

14. The photosensitising composition of claim 13, wherein the at least one alcohol includes a monohydric alcohol.

15. The photosensitising composition of claim 13, at least one photosensitising compound is a phenothiazine dye.

16. The photosensitising composition of claim 13, wherein the at least one photosensitising compound is selected from the group consisting of toluidine blue, methylene blue, arianor steel blue, tryptan blue, crystal violet, azure blue cert, azure B chloride, azure II, azure A chloride, azure B tetrafluoroborate, thionin, azure A eosinate, azure B eosinate, azure mix sicc., azure II eosinate, haematoporphyrin HCI, haematoporphyrin ester, aluminium disulphonated phthalocyanine, chlorins, photoactive fullerenes, aminolevulinic acid (ALA), bacteriochlorins, phthalocyanines, pheophorbides, purpurins, naphthalocyanines, indocyanine green, and mixtures thereof.

17. The photosensitising composition of claim 13, wherein the at least one surfactant is polyethylene glycol and the at least one alcohol is ethanol.

18. The photosensitising composition of claim 17, wherein a ratio of the volume of the polyethylene glycol to ethanol to water is 30:20:50.

* * * * *